US008545447B2

(12) United States Patent
Demarais et al.

(10) Patent No.: US 8,545,447 B2
(45) Date of Patent: Oct. 1, 2013

(54) MECHANICAL PUMP FOR REMOVAL OF FRAGMENTED MATTER AND METHODS OF MANUFACTURE AND USE

(75) Inventors: Denise M. Demarais, Los Gatos, CA (US); Stephen A. Leeflang, Sunnyvale, CA (US); Michael A. Evans, Palo Alto, CA (US); Gwendolyn A. Watanabe, Sunnyvale, CA (US); John C. Tanner, III, Los Angeles, CA (US); Christian S. Eversull, Palo Alto, CA (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/589,431

(22) Filed: Aug. 20, 2012

(65) Prior Publication Data
US 2012/0316586 A1    Dec. 13, 2012

Related U.S. Application Data

(63) Continuation of application No. 13/278,210, filed on Oct. 21, 2011, now Pat. No. 8,277,470, which is a continuation of application No. 12/638,149, filed on Dec. 15, 2009, now Pat. No. 8,062,258, which is a continuation of application No. 10/797,482, filed on Mar. 9, 2004, now Pat. No. 7,655,016, which is a continuation-in-part of application No. 10/680,367, filed on Oct. 6, 2003, now Pat. No. 6,945,977, and a continuation-in-part of application No. 09/590,915, filed on Jun. 9, 2000, now Pat. No. 6,702,830, said application No. 10/680,367 is a continuation of application No. 10/162,276, filed on Jun. 3, 2002, now Pat. No. 6,660,014, which is a continuation of application No. 09/454,517, filed on Dec. 6, 1999, now Pat. No. 6,454,775.

(60) Provisional application No. 60/154,752, filed on Sep. 17, 1999.

(51) Int. Cl.
*A61M 5/178* (2006.01)

(52) U.S. Cl.
USPC .......................................................... 604/159

(58) Field of Classification Search
USPC .................. 604/159, 113, 114, 127, 128, 115
See application file for complete search history.

(56) References Cited

U.S. PATENT DOCUMENTS

| 3,320,957 A | 5/1967 | Sokolik |
| 4,447,227 A | 5/1984 | Kotsanis |

(Continued)

FOREIGN PATENT DOCUMENTS

| WO | WO 95/21576 | 8/1995 |
| WO | WO 96/01591 | 1/1996 |

(Continued)

OTHER PUBLICATIONS

Schmitz-Rode et al., "New Device for Percutaneous Fragmentation of Pulmonary Emboli" Radiology (1991) 180:135-137.

(Continued)

*Primary Examiner* — Manuel Mendez
(74) *Attorney, Agent, or Firm* — Thomas M. Johnston, Esq.

(57) ABSTRACT

Material transport catheters and methods for their use rely on rotation of an impeller within a catheter body and a clearing element for preventing buildup of materials at the opening of the catheter body. The impeller preferably comprises an inner tube or shaft having a helical rotor fainted over an outer surface thereof. The clearing element may comprise a free end of a structure near the distal end of the catheter body for disrupting clot, wherein the free end of the structure extends into the distal opening of the catheter body to break up materials as the impeller is rotated. Alternatively, the clearing element may comprise a cutting member disposed at the distal opening of the catheter body.

22 Claims, 18 Drawing Sheets

(56) References Cited

U.S. PATENT DOCUMENTS

| | | |
|---|---|---|
| 4,621,636 A | 11/1986 | Fogarty |
| 4,646,736 A | 3/1987 | Auth |
| 4,665,906 A | 5/1987 | Jervis |
| 4,681,106 A | 7/1987 | Kensey et al. |
| 4,732,154 A | 3/1988 | Shiber |
| 4,737,153 A | 4/1988 | Shimamura et al. |
| 4,762,130 A | 8/1988 | Fogarty et al. |
| 4,771,774 A | 9/1988 | Simpson et al. |
| 4,819,634 A | 4/1989 | Shiber |
| 4,842,579 A | 6/1989 | Shiber |
| 4,857,046 A | 8/1989 | Stevens et al. |
| 4,878,903 A | 11/1989 | Mueller |
| 4,883,458 A | 11/1989 | Shiber |
| 4,886,490 A | 12/1989 | Shiber |
| 4,894,051 A | 1/1990 | Shiber |
| 4,895,166 A | 1/1990 | Farr et al. |
| 4,923,462 A | 5/1990 | Stevens |
| 4,926,858 A | 5/1990 | Gifford, III et al. |
| 4,957,482 A | 9/1990 | Shiber |
| 4,966,604 A | 10/1990 | Reiss |
| 4,979,939 A | 12/1990 | Shiber |
| 5,002,553 A | 3/1991 | Shiber |
| 5,007,896 A | 4/1991 | Shiber |
| 5,011,488 A | 4/1991 | Ginsburg |
| 5,024,651 A | 6/1991 | Shiber |
| 5,030,201 A | 7/1991 | Palestrant |
| 5,041,082 A | 8/1991 | Shiber |
| 5,041,093 A | 8/1991 | Chu |
| 5,047,040 A | 9/1991 | Simpson et al. |
| 5,078,722 A | 1/1992 | Stevens |
| 5,092,844 A | 3/1992 | Schwartz et al. |
| 5,100,423 A | 3/1992 | Fearnot |
| 5,112,292 A | 5/1992 | Hwang et al. |
| 5,116,352 A | 5/1992 | Schnepp-Pesch et al. |
| 5,129,910 A | 7/1992 | Phan et al. |
| 5,135,531 A | 8/1992 | Shiber |
| 5,163,910 A | 11/1992 | Schwartz et al. |
| 5,180,376 A | 1/1993 | Fischell |
| 5,192,268 A | 3/1993 | Shiber |
| 5,226,909 A | 7/1993 | Evans et al. |
| 5,306,244 A | 4/1994 | Shiber |
| 5,322,572 A | 6/1994 | Wanlass |
| 5,330,484 A | 7/1994 | Günther et al. |
| 5,334,211 A | 8/1994 | Shiber |
| 5,419,774 A | 5/1995 | Willard et al. |
| 5,423,799 A | 6/1995 | Shiu |
| 5,443,443 A | 8/1995 | Shiber |
| 5,462,529 A | 10/1995 | Simpson et al. |
| 5,485,042 A | 1/1996 | Burke |
| 5,501,694 A | 3/1996 | Ressemann et al. |
| 5,507,795 A | 4/1996 | Chiang et al. |
| 5,540,707 A | 7/1996 | Ressemann et al. |
| 5,556,408 A | 9/1996 | Farhat |
| 5,569,275 A | 10/1996 | Kotula et al. |
| 5,569,277 A | 10/1996 | Evans et al. |
| 5,569,284 A | 10/1996 | Young et al. |
| 5,571,122 A | 11/1996 | Kelly et al. |
| 5,597,378 A | 1/1997 | Jervis |
| 5,616,149 A | 4/1997 | Barath |
| 5,630,806 A | 5/1997 | Inagaki et al. |
| 5,632,755 A | 5/1997 | Nordgren et al. |
| 5,643,199 A | 7/1997 | Rowland et al. |
| 5,643,229 A | 7/1997 | Sinaiko |
| 5,653,696 A | 8/1997 | Shiber |
| 5,681,335 A | 10/1997 | Serra et al. |
| 5,688,234 A | 11/1997 | Frisbie |
| 5,690,641 A | 11/1997 | Sorensen et al. |
| 5,695,507 A | 12/1997 | Auth et al. |
| 5,766,191 A | 6/1998 | Trerotola |
| 5,795,322 A | 8/1998 | Boudewijn |
| 5,843,031 A | 12/1998 | Hermann et al. |
| 5,873,882 A | 2/1999 | Straub et al. |
| 5,876,414 A | 3/1999 | Straub |
| 5,899,850 A | 5/1999 | Ouchi |
| 5,904,698 A | 5/1999 | Thomas et al. |
| 5,911,734 A | 6/1999 | Tsugita et al. |
| 5,928,186 A | 7/1999 | Homsma et al. |
| 5,947,940 A | 9/1999 | Beisel |
| 5,947,985 A | 9/1999 | Imran |
| 5,954,737 A | 9/1999 | Lee |
| 5,972,019 A | 10/1999 | Engelson et al. |
| 6,001,112 A | 12/1999 | Taylor |
| 6,036,708 A | 3/2000 | Sciver |
| 6,066,152 A | 5/2000 | Strauss et al. |
| 6,066,158 A | 5/2000 | Engelson et al. |
| 6,090,118 A | 7/2000 | McGuckin, Jr. |
| 6,454,775 B1 * | 9/2002 | Demarais et al. ............ 606/128 |
| 6,660,014 B2 | 12/2003 | Demarais et al. |
| 6,702,830 B1 | 3/2004 | Demarais et al. |
| 6,945,977 B2 | 9/2005 | Demarais et al. |
| 7,655,016 B2 | 2/2010 | Demarais et al. |
| 8,062,258 B2 | 11/2011 | Demarais et al. |
| 2002/0151906 A1 | 10/2002 | Demarais et al. |
| 2004/0082962 A1 | 4/2004 | Demarais et al. |
| 2004/0219028 A1 | 11/2004 | Demarais et al. |
| 2010/0185208 A1 | 7/2010 | Demarais et al. |
| 2012/0035594 A1 | 2/2012 | Demarais et al. |

FOREIGN PATENT DOCUMENTS

| | | |
|---|---|---|
| WO | WO 96/29941 | 10/1996 |
| WO | WO 98/38929 | 9/1998 |
| WO | WO 99/44510 | 9/1999 |
| WO | WO 99/44542 | 9/1999 |
| WO | WO 00/41762 | 7/2000 |

OTHER PUBLICATIONS

Sharafuddin et al., "Current Status of Percutaneous Mechanical Thrombectomy. Part 1. General Principles" Journal of Vascular and Interventional Radiology (1997) 8(6):911-921.

Wampler et al., "Circulatory Support of Cardiac Interventional Procedures With the Hemopump Cardio Assist System" Cardiology (1994) 84(3):194-201.

U.S. Appl. No. 09/454,517, filed Dec. 6, 1999, Demarais et al., Office Action, Oct. 1, 2001, Mar. 28, 2002, Notice of Allowance, Jun. 18, 2002.

* cited by examiner

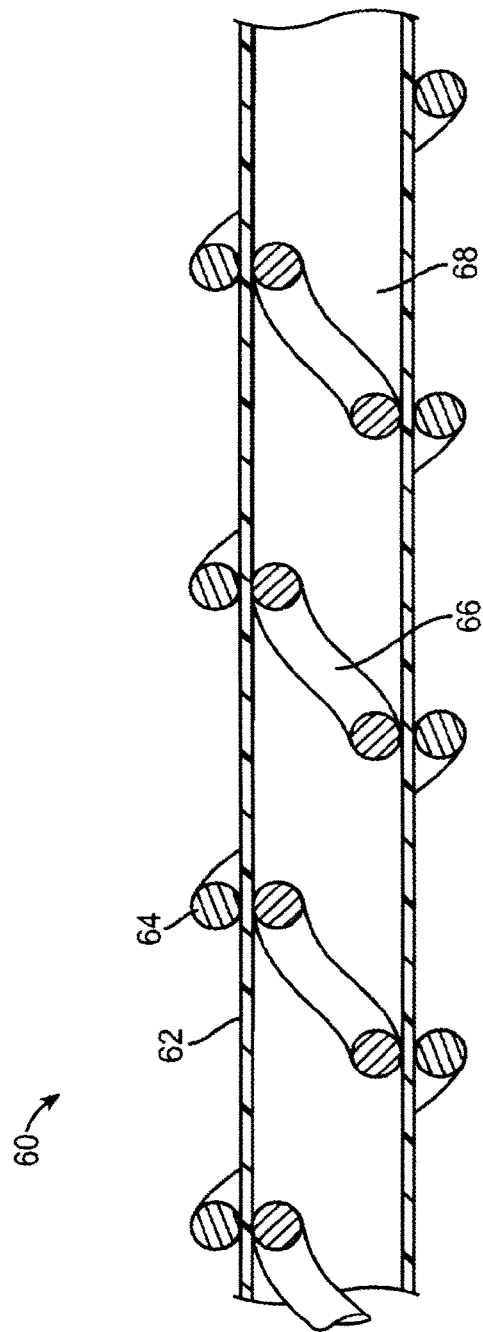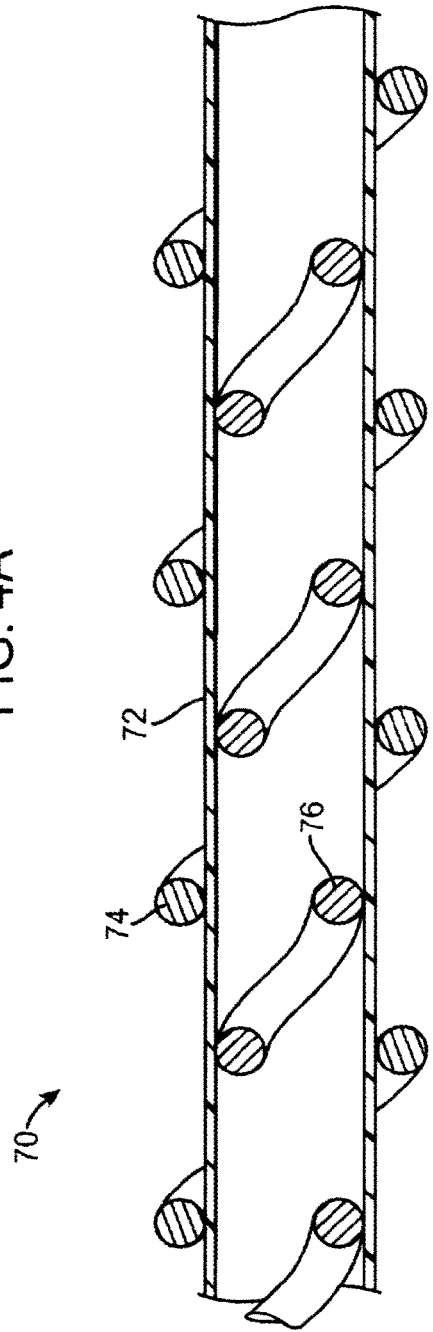

MECHANICAL PUMP FOR REMOVAL OF FRAGMENTED MATTER AND METHODS OF MANUFACTURE AND USE

CROSS-REFERENCE TO RELATED APPLICATIONS

This application is a continuation of U.S. patent application Ser. No. 13/278,210, filed on Oct. 21, 2011, which is a continuation of U.S. patent application Ser. No. 12/638,149, filed on Dec. 15, 2009, now U.S. Pat. No. 8,062,258, which is a continuation of U.S. patent application Ser. No. 10/797,482, filed on Mar. 9, 2004, now U.S. Pat. No. 7,655,016, which is a continuation-in-part of U.S. patent application Ser. No. 09/590,915, filed on Jun. 9, 2000, now U.S. Pat. No. 6,702,830, which claims the benefit under 35 U.S.C. §119(e) of U.S. provisional patent application Ser. No. 60/154,752, filed on Sep. 17, 1999. Application Ser. No. 10/797,482, filed on Mar. 9, 2004, now U.S. Pat. No. 7,655,016 is also a continuation-in-part of U.S. patent application Ser. No. 10/680,367, filed on Oct. 6, 2003, now U.S. Pat. No. 6,945,977, which is a continuation of U.S. patent application Ser. No. 10/162,276, filed on Jun. 3, 2002, now U.S. Pat. No. 6,660,014, which is a continuation of U.S. patent application Ser. No. 09/454,517, filed on Dec. 6, 1999, now U.S. Pat. No. 6,454,775. The full disclosures of the priority applications are incorporated herein by reference in their entireties.

TECHNICAL FIELD

The present invention relates generally to medical apparatus and methods and more particularly to devices and methods for removal of unwanted tissue such as thrombus, atheroma, fluid, polyps, cysts or other obstructive matter from body lumens, such as blood vessels, ureters, bile ducts or fallopian tubes.

BACKGROUND

Currently, there are many clinical approaches to removing unwanted material, many of which are performed surgically, wherein the treatment site is accessed directly through a surgical incision.

In recent years, a variety of catheter devices have been developed for use in intraluminal and intravascular procedures for fragmentation and removal of obstructive matter, such as blood clots, thrombus, atheroma, and the like, from blood vessels. More recently, devices that can be inserted percutaneously through a puncture in the skin have been developed to make the procedures less invasive. For example, a catheter device is inserted into a blood vessel at an access site located some distance away from the intended treatment site, and is then advanced through the vessel lumen until the treatment site is reached. In most instances this approach is performed "over-the-wire," a technique that requires the physician to first place a guidewire device into the vessel lumen over which a larger catheter device can be tracked.

These techniques may employ various devices to fragment the unwanted clot or tissue from blood vessels such as rotating baskets or impellers as described in U.S. Pat. Nos. 5,766,191 and 5,569,275, cutters as described in U.S. Pat. No. 5,501,694, and high pressure fluid infusion to create a Venturi effect as described in U.S. Pat. No. 5,795,322. Other devices rely on the principles of the Archimedes-type screw, such as a one-piece solid machined screw to break up and/or remove clot.

In many instances, the luminal treatment techniques include infusing the vessel or treatment site with fluid (saline or a thrombolytic agent) to assist in breaking up the clot or tissue into a particle size that can then be aspirated through a lumen of the treatment device or using a secondary catheter hooked up to a source of vacuum/suction. Depending on the method of fragmentation and the consistency of the clot or tissue, the particle size can vary. If the material is not thoroughly fragmented, the larger particles can build up in the catheter and block the aspiration lumen.

While these catheters and techniques have been fairly successful, there is a need for improved devices for more efficiently evacuating fragmented material from the vessel or body lumen in order to overcome the difficulties of continued fluid infusion and material build up that blocks the aspiration lumen. Furthermore, it would be desirable to have devices that allowed aspiration of larger particles of fragmented material, thereby reducing procedure time. Preferably, such improved devices will have a low profile to enable percutaneous use, and will be flexible and torqueable to enable their use in tortuous lumens. Furthermore, such devices will preferably be designed to be placed over a guidewire and will be structured to mechanically translate and transport the fragmented material by directly pumping it through the catheter shaft. Optionally, the devices should include mechanisms for infusing materials, such as thrombolytic and other therapeutic agents, as well as disrupting the occlusive materials.

At least some of these objectives will be met by the design and use of the present invention.

U.S. Pat. No. 5,556,408 describes an atherectomy cutter employing a vacuum source for removal of loose stenotic material and other debris from a vessel. Removal of thrombus by a rotating core wire on a drive shaft is described in U.S. Pat. No. 5,695,507 and fragmentation and removal of tissue using high pressure liquid is described in U.S. Pat. No. 5,795,322. U.S. Pat. No. 4,923,462 describes a coiled wire coated with Teflon and used as a drive shaft to rotate a catheter. Furthermore, U.S. Pat. No. 5,334,211 describes a coiled guidewire used to stabilize an atherectomy device. Patents describing atherectomy catheters with rotating helical pumping elements in U.S. Pat. Nos. 4,732,154; 4,886,490; 4,883,458; 4,979,939; 5,041,082; 5,135,531; 5,334,211; 5,443,443; and 5,653,696. A rotary thrombectomy catheter having an inner helical blade is commercially available under the tradename Straub Rotarex® from Straub Medical AG, as described in a brochure with a copyright of August 1999. Use and construction of the Straub Rotarex® also appears to be described in Schmitt et al. (1999) Cardiovasc. Intervent. Radiol. 22:504-509 and in U.S. Pat. Nos. 5,876,414 and 5,873,882. Other patents of interest include U.S. Pat. Nos. 4,737,153; 4,966,604; 5,047,040; 5,180,376; 5,226,909; 5,462,529; 5,501,694; 5,569,275; 5,630,806; 5,766,191, 5,843,031; 5,911,734; 5,947,940; and 5,972,019; as well as published PCT applications WO 99/56801; WO 99/56638; and WO 98/38929. Motor drive units for catheters and other devices are described in U.S. Pat. Nos. 4,771,774 and 5,485,042.

SUMMARY

According to the present invention, improved apparatus and methods are provided for transporting material between a target site in a body lumen of a patient and a location external to the patient. In some cases, the materials will be transported from the target site to the external location, which methods will generally be referred to as aspiration. In other cases, the material may be transported from the external location to the target site within the body lumen, which methods will generally referred to as infusion. In still other cases, materials may be simultaneously transported from the external location to the internal target site and transported away from the internal target site to the external location, referred to as circulation. In all cases, the material transport will be enhanced by rotation of an impeller disposed in a lumen of a catheter. The impeller will usually comprise a tubular or solid shaft having a helical rotor extending at least partially over an exterior surface thereof. Thus, rotation of the impeller will pump the material in the manner of an "Archimedes screw."

In addition to such mechanical pumping, the methods and apparatus of the present invention may rely on supplemental pressurization of the catheter lumen being used to transport the material. In particular, for infusion, the liquid or other material to be introduced may be supplied under pressure, typically in the range from 0.1 psi to 10,000 psi, usually in the range from 5 psi to 350 psi. Conversely, in the case of aspiration, a vacuum may be applied to the catheter lumen, usually from 1 mmHg to 760 mmHg, usually from 5 mmHg to 760 mmHg.

The methods and apparatus of the present invention will be particularly suitable for use in medical procedures for removing occlusive and other substances from body lumens, such as blood clots, thrombus, and the like, from blood vessels. Catheters according to the present invention will be suitable for percutaneous introduction or introduction by a surgical cutdown to the blood vessel or other body lumen. Usually, the catheters will then be advanced to a remote target site where the treatment is performed. Preferably, the catheters of the present invention will be introduced over a guidewire in a so-called "over-the-wire" technique, although use of a guidewire will not always be required. Optionally, the apparatus of the present invention may be used in conjunction with a variety of other interventional catheters, particularly for intravascular treatments. For example, the material transport catheters of the present invention may be used to infuse thrombolytic and other therapeutic agents and/or aspirate fragmented clot, thrombus, and other occlusive materials in conjunction with angioplasty, atherectomy, laser ablation, embolectomy, endarterectomy and other known intravascular interventions. In particular, the material transport catheters of the present invention may be used in the procedures described in copending U.S. patent application Ser. No. 09/454,517, which has previously been incorporated herein by reference.

In a first aspect of the present invention, an over-the-wire material transport catheter comprises a catheter body having a proximal end, a distal end, and a lumen therebetween. An impeller is rotatably disposed in the lumen of the catheter body, and the impeller includes a tubular shaft having a central guidewire lumen therethrough. A helical rotor extends at least partially over an exterior surface of the tubular shaft, and it is intended that the material transport catheter be introduced over a guidewire in a conventional manner. Moreover, the impeller will usually be rotated over the guidewire, i.e., while the guidewire remains in place in the central guidewire lumen of the impeller, during use of the catheter for aspiration and/or infusion. Optionally, the material transport catheter may further comprise a material capture device, such as a funnel structure, a macerator, or the like, at or near the distal end of the catheter body. Alternatively, the distal end of the catheter body may be substantially free from surrounding structure so that a desired material may be infused and/or aspirated directly through one or more ports in the catheter body at or near its distal end.

In a second aspect, a selective infusion-aspiration catheter constructed in accordance with the principles of the present invention comprises a catheter body having a proximal end, a distal end, and a lumen therebetween. An impeller is rotatably disposed in the lumen of the catheter body, and a driver is provided which is coupleable to the impeller. By "coupleable," it is meant either that the driver and impeller are permanently connected, or more usually, that the driver is a separate component but that the driver and impeller are adapted to selectively mate and permit the driver to rotate the impeller while the impeller remains disposed in the catheter body lumen. The driver will be adapted to selectively rotate the impeller in either a first direction to induce aspiration to the catheter body lumen or in a second direction to induce infusion through the catheter body lumen. In this way, the selective infusion-aspiration catheter can be used either for infusion or aspiration depending on the particular circumstances encountered. The selective infusion-aspiration catheter may further comprise a material capture device disposed at or near the distal end of the catheter body, such as a funnel structure, a macerator, or the like. Alternatively, the distal end of the catheter body may be substantially free from surrounding structure so that material may be aspirated and/or infused through one or more ports located at or near the distal end of the catheter body.

In a third aspect of the present invention, a circulation catheter comprises a catheter body having a proximal end, a distal end, and at least one lumen extending between the proximal end and the distal end. A first impeller is arranged in a lumen of a catheter body to aspirate materials from the distal end to the proximal end of the catheter body when the impeller is rotated. A second impeller is arranged in a lumen of the catheter body to infuse materials from the proximal end of the catheter body to the distal end of the catheter body when the second impeller is rotated. Since the circulation catheter includes two separate impellers, it is possible to rotate the impellers simultaneously so that material can be infused to a target location within a body lumen and simultaneously aspirated from that target location. For example, the circulation catheter may be used to introduce thrombolytic or other therapeutic agent to a blood vessel and to simultaneously or sequentially remove the lysed clot, thrombus, and other materials from the blood vessel. Suitable thrombolytic and other agents include GPIIIb/IIa antagonists, tissue plasminogen activator (tPA), calcium dissolving agents, urokinase (proUK), heparinized saline, and the like. Other therapeutic agents include fibrinolytics, anti-coagulants, antiplatlet drugs, anti-thrombin, gene therapy agents, chemotherapeutic agents, brachytherapy agents, and the like. Optionally, the first impeller and second impeller may terminate at spaced-apart ports along the length of the catheter body so that the thrombolytic or other agent will be assured of having a minimum residence tune within the blood vessel prior to being aspirated. Further optionally, the first impeller and second impeller may be disposed in separate lumens within the catheter body. In such cases, both impellers will usually comprise a tubular or solid shaft having a helical rotor formed over the outer surface thereof. Rotation of the shaft thus selectively infuses or aspirates material through the associated catheter lumen. Alternatively, the first and second impellers may comprise a common tubular shaft where a first helical rotor is mounted over the exterior surface and a second helical rotor is mounted over an interior surface of the shaft lumen. By counterwinding the two helical rotors, it will be appreciated that the outer rotor will transport material in a first direction while the inner rotor transports the material in opposite direction. Thus, material may be infused through the annular lumen formed between the outside of the tubular shaft and the catheter body lumen and aspirated back through the interior of the tubular shaft, or vice versa.

As with the prior embodiments, the circulation catheter may further comprise a material capture device disposed at the distal end of the catheter body, such as a funnel structure, a macerator, or the like. Alternatively, the catheter body may be substantially free from surrounding structure.

In a fourth aspect of the present invention, a mechanical pump for use in a medical device comprises an elongate hollow, flexible inner tube having a proximal end, a distal end, and a central guidewire lumen. A first coiled (helical) rotor element having a distal end and a proximal end is disposed over an outer surface of the inner tube. A jacket secures the coiled rotor element to the outer surface to complete the mechanical pump. The mechanical pump structure may then be used in the lumen of a catheter body or elsewhere in order to provide a pumping action in the manner of an Archimedes screw. Preferably, the inner tube has an outer diameter in the range from 0.5 mm to 5 mm, usually from 1 mm to 2 mm. The assembled coiled rotor will have a width in the diameter from 0.5 mm to 10 mm, preferably from 0.5 mm to 3 mm, and a pitch over the inner tube in the range from 1 turns/cm to 50 turns/cm, preferably from 3 turns/cm to 10 turns/cm. Optionally, the mechanical pump may further comprise a second coiled rotor element disposed over an inner surface of the central lumen of the inner tube. The first and second coiled rotors will usually be counterwound so that the pump may direct flow in both a distal direction and a proximal direction when the inner tube is rotated in a single direction. Alternatively, the first and second coiled rotors may be co-wound so that the pump may provide an increased flow through a catheter lumen when the pump is rotated in either direction. In a particular aspect of the present invention, a distal portion of the coiled rotor may be unattached to the outer surface of the inner tube so that said unattached portion forms or provides a "whip" element as the pump is rotated. The whip element will be suitable for mechanically disrupting clot, thrombus, or other occlusive materials when the pump is rotated in a body lumen. Alternatively, the whip may be used to mix the thrombolytic or other agents (as set forth above) which are being introduced by the pump in a blood vessel or other body lumen.

The mechanical pump just described may be fabricated by providing a hollow flexible tube, placing a resilient coiled rotor over an outer surface of the tube, and forming a jacket over at least a portion of the outer surface of the tube. In this way, the coiled rotor is secured to the outer surface of the flexible tube. Such a fabrication method is inexpensive and provides a high quality product. Placing the resilient coil over an outer surface of the inner tube may comprise winding the coil over the surface to successively place individual turns of the coil as the inner tube is rotated. Alternatively, a preformed coil may be partially "unwound" to increase its diameter and permit the coil to be located over the exterior surface of the inner tube. When in the proper location, the coil may be allowed to rewind over the surface to provide an interference fit. The interference fit can be enhanced by heating the wire. Preferably, the coil is then secured to the outer surface of the inner tube by forming or placing a jacket over the structure. For example, the jacket formed by dip coating the assembly of the tube and rotor(s) into an appropriate curable liquid polymer, such as nylon, polyurethane, polyimide, polyamide, PTFE, FEP, and the like. The coating can then be heated and/or radiation cured to induce cross-linking Further, alternatively, the jacket may be placed by providing a heat shrinkable polymeric tube or sleeve, placing said tube or sleeve over the combination of inner tube and helical rotor, and then shrinking the jacket over the inner tube and coiled rotor to hold the two together. Further alternatively, the jacket may be formed by extruding a polymeric material directly over the inner tube and coil, or by vapor deposition or spray coating. In an alternative embodiment, the coil may be attached to the inner tube by an adhesive.

The present invention still further comprises methods for transporting materials between a target site in a body lumen of a patient in a location external to the patient. The distal end of the catheter is introduced to the target site over a guidewire. First impeller is rotated over the guidewire within a lumen in the catheter to transport material between the distal end of the catheter and a proximal end of the catheter. The material may be selectively transported in a first direction by rotating the impeller for aspiration, and a vacuum may be applied to the lumen of the catheter to assist in transporting material from the distal end. Alternatively, the impeller may be selectively rotated to transport material from the proximal end of the catheter through the catheter lumen to the distal end of the catheter, e.g., to infuse materials. In such instances, the materials may be provided to the catheter lumen under pressure to assist in transporting the material through the catheter lumen to the distal end of the catheter.

In some instances, the direction in which the impeller is rotated may be changed. Thus, at one time, the impeller may be rotated in a first direction to infuse materials to the target site within a body lumen. At a subsequent time, the impeller may be rotated in the opposite direction to remove or aspirate materials from the same target site.

In still another instance, a second impeller may be provided in the catheter and rotated to selectively transport material between the proximal end of the catheter and the distal end of the catheter. By simultaneously rotating the first impeller to transport material in an opposite direction, a circulation of material may be established.

In still another instance, first and second impellers may comprise counterwound helical rotors mounted on a common tubular member. In such an instance, rotation of the tubular member in one direction will cause a first rotor to infuse materials to the target site while the second rotor aspirates materials from the same target site. In all instances, infusion and aspiration may be assisted by applying pressure or a vacuum, as appropriate.

The first impeller will conveniently be mounted on the outside of the tubular member, e.g., by any of the methods described above for placing a coiled rotor over a shaft member. The second impeller will usually be in the form of a helical rotor disposed within the lumen of the tubular member. The helical rotor may be "wound down" to assume a low profile, inserted into the tubular member lumen, and then allowed to unwind to provide an interference fit with the lumen wall. The coil may be further secured or attached to the lumen wall by any of the methods described above.

In still another aspect of the present invention, a method for selectively infusing and aspirating materials between a target site in a body lumen or patient and the location external to the patient, comprises introducing a distal end of the catheter to the target site. An impeller within the lumen of the catheter is rotated in a first direction to infuse material to the target site. Sequentially, the impeller is rotated in a second direction to aspirate material to the target site. Such infusion and aspiration can be particularly useful with the delivery of thrombolytic agents to blood vessels and the removal of lysed clot from those blood vessels.

In yet still another aspect of the present invention, a method for circulating materials through a target site in a body lumen of a patient comprises introducing a distal end of the catheter to the target site. A first impeller within the lumen of the catheter is rotated to transport material to the target site. A second impeller within a lumen of the catheter is rotated to transport material away from the target site. The first and second impellers may be located within separate lumens within the catheter, or alternatively, may be located within the same lumen within the catheter. In latter case, first and second impellers will usually comprise a flexible inner tube having a first helical rotor formed over an outer surface thereof and a second helical rotor formed over an inner luminal surface thereof. The first and second helical rotors are counterwound so that rotation of the inner tube in one direction will cause flow over the tube in a first direction and flow through the tube in the opposite direction.

In particular, the present invention provides an elongate mechanical pump component that can be used in an aspiration catheter as a stand alone device, or as part of the shaft construction of a therapeutic device to remove the material fragmented by the working end of the therapeutic device. The mechanical pump component is hollow, forming a guidewire lumen to allow it to be compatible with use over a guidewire, or with devices requiring a guidewire.

In an exemplary embodiment the pump device is formed from a resilient wire coil, wound along the length of a hollow flexible polymer tube, and bonded or attached thereto by an outer polymer coating that cross links or heat bonds to the inner tube. The coil member can be of various geometric cross sectional shapes. The outer polymer coating is preferably made of a thinner wall plastic than the inner hollow tube to assist in the attachment process. The thin wall coating also allows the struts of the coil member to protrude from the surface of the inner tube which, when rotated, provide the pumping action.

The present invention may also incorporate an outer sheath surrounding the mechanical pump to form a catheter device. The catheter device would be attached to a rotating motor drive unit (MDU) at the proximal end allowing the mechanical pump component to rotate at varying speeds, while the catheter sheath remains stationary. Optionally, the MDU can selectively drive the pump element in a clockwise or counterclockwise direction relative to the longitudinal axis of the device. In use, any material to be removed is evacuated through the annular space between the mechanical pump and the outer sheath and is moved proximally by the rotating coils of the mechanical pump.

In another aspect of the invention, a circulation catheter having a clearing element is disclosed. The catheter generally comprises: a catheter body having a proximal end, a distal end, and a lumen therebetween, the lumen forming a distal opening at the distal end of the catheter body; an impeller rotatably disposed in the lumen of the catheter body to aspirate materials from the distal end to the proximal end of the catheter body; and a clearing element disposed at the distal opening of the catheter body to prevent the materials from accumulating at the distal opening. In general, the clearing element spins relative to the catheter body to clear the distal opening of the catheter body as the shaft is rotated.

The circulation catheter may further comprise a material capture device, such as a macerator disposed at the distal end of the catheter body. In some embodiments, the macerator comprises a distal end and a proximal end, wherein the proximal end of the macerator extends into the distal opening of the catheter body to form the clearing element.

In another embodiment, the clearing element comprises a cutting member coupled to the impeller at or near the distal opening. The cutting member may be attached to the proximal end of the macerator. Alternatively, the cutting member is attached to a shaft coupled to the impeller.

In one aspect of the invention, a method for transporting materials between a target site in a body lumen, and a location external to the patient comprise: introducing a distal end of a catheter to the target site; rotating an impeller within a lumen of the catheter to aspirate material from the target site; and clearing an opening of the lumen at the distal end of the catheter body to prevent the material from accumulating at the opening.

Generally, clearing the opening comprises rotating a clearing element inside the distal opening of the catheter body. In some embodiments, the impeller has shaft and a helical rotor, wherein rotating the impeller further comprises rotating a macerator attached at a distal end of the impeller shaft, and wherein clearing the opening of the lumen comprises spinning a proximal end of the macerator inside the distal opening of the catheter body.

In another embodiment the clearing element is coupled to the impeller, and the clearing element is spun inside the distal opening of catheter body as the impeller is rotated to clear the opening of the lumen. The clearing element may comprises a cutting disk that is attached to the shaft or rotor of the impeller or the proximal end of the macerator.

BRIEF DESCRIPTION OF THE DRAWINGS

FIGS. 4A and 4B illustrate cross-sectional views of alternative constructions of the mechanical pump of FIGS. 3A-3C.

DETAILED DESCRIPTION

Figure 1:
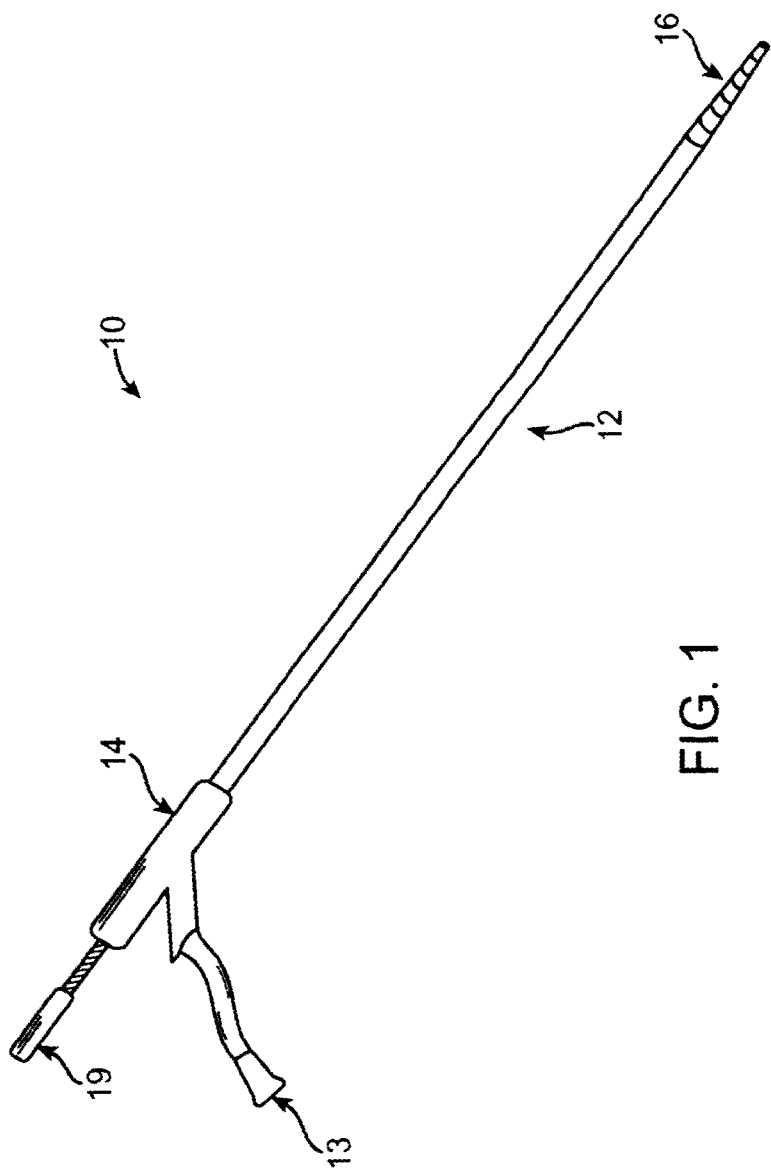
FIG. 1 illustrates a first embodiment of material transport catheter constructed in accordance with the principles of the present invention.

An exemplary material transport catheter in the form of a mechanical aspiration device constructed in accordance with the present invention is illustrated in FIG. 1. The aspirating device 10 comprises a catheter body 12, having an adapter "Y" hub 14 at a proximal end thereof, an aspiration/injection tube 13 on the hub 14, an impeller 16 having a helical rotor to define a "coiled pump member" operatively coupled to a motor drive unit (not shown) by drive shaft and spindle assembly 19. Optionally, the device may include a hemostasis sheath (not shown) either as part of the catheter sleeve, or as a separate device through which the aspirating device is inserted. Depending on the desired clinical result, the impeller 16 can be recessed within the catheter outer sheath 12, flush with the end of the catheter outer sheath, or extend distally of the catheter outer sheath, by varying the length of the coiled pump member, the catheter outer sheath, or both.

Figure 1A:
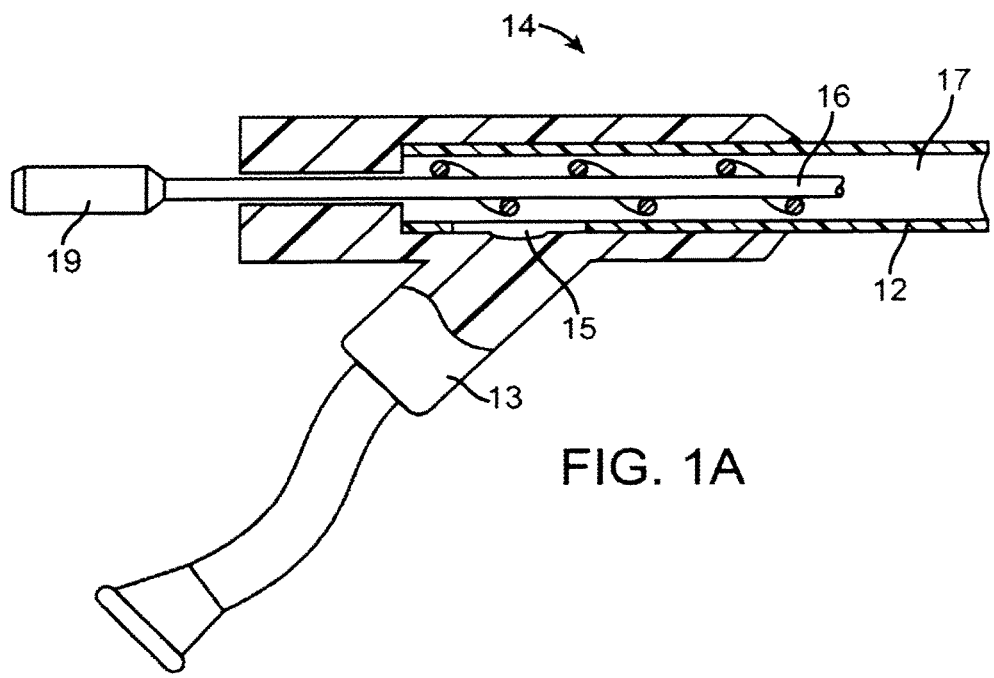
FIG. 1A is a detailed view of the proximal end of the catheter of FIG. 1, shown in partial cross-section.

As shown in FIG. 1A, the catheter body 12 has a port 15 which is aligned with the aspiration/injection tube 13 so that materials may be removed from the lumen 17 of the catheter body 12 and/or infused into the lumen. The coiled pump member continues from the distal end of the catheter body 12 (as shown in FIG. 1) all the way into the proximal hub 14 so that material may be transported to or from the distal end depending on the direction of rotation of the coiled pump member 16.

Figure 1B:
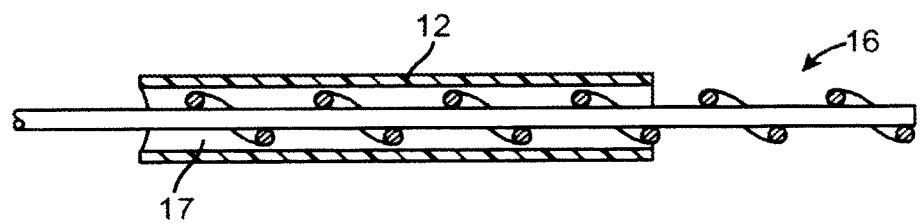
FIG. 1B is a detailed view of the distal end of the catheter of FIG. 1, shown in cross-section.
Figure 1C:
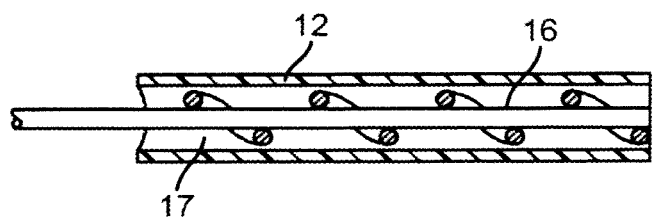
FIG. 1C is an alternative distal end of the catheter of FIG. 1, shown in cross-section.

FIG. 1B is a cross-sectional view of the distal end of the catheter body 12, showing the entry of coiled pump member 16 into the lumen 17. Alternatively, the coiled pump member 16 could terminate at (or before) the distal end of the catheter body 12, as shown in FIG. 1C. In such an embodiment, infusion/aspiration ports could be provided along the distal end of the catheter body 12 (not illustrated).

Figure 1D:
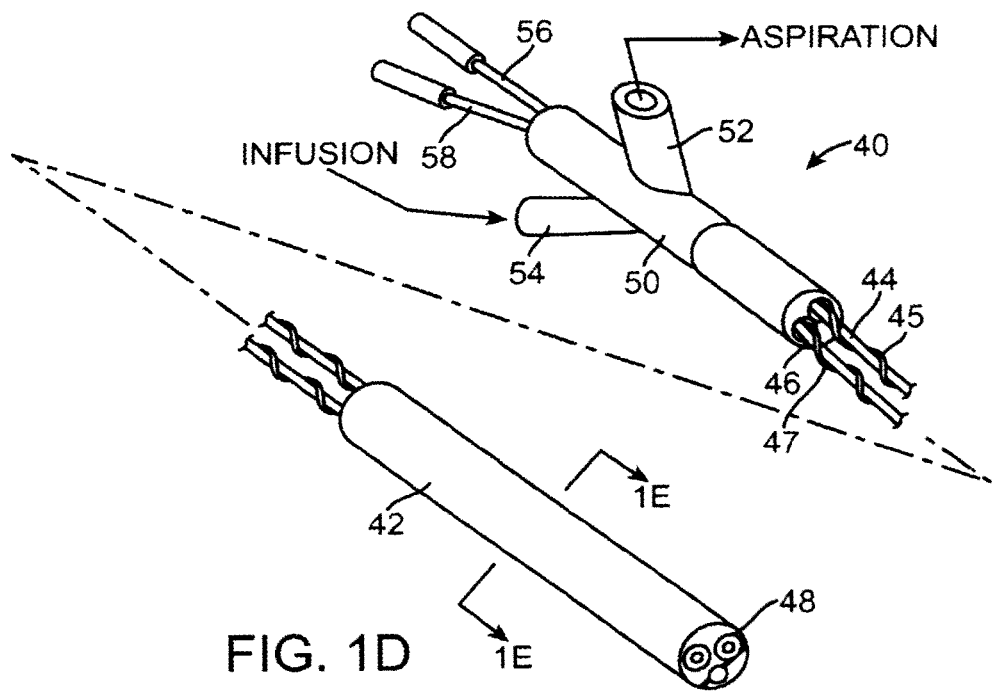
FIG. 1D illustrates a second embodiment of a material transport catheter constructed in accordance with the principles of the present invention.
Figure 1E:
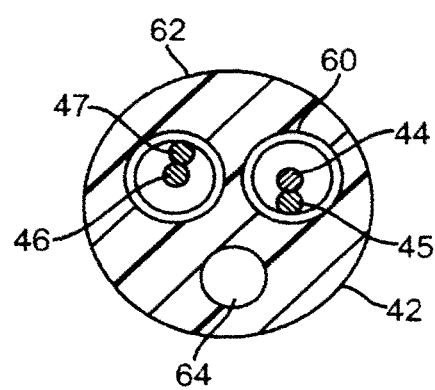
FIG. 1E is a cross-sectional view taken along the line 1E-1E on FIG. 1D.

Referring now to FIGS. 1D and 1E, a second embodiment of a material transport catheter constructed in accordance with the principles of the present invention will be described. Material transport catheter 40 comprises a catheter body 42 which may be adapted for introduction to the vasculature or other body lumens of a patient. The catheter body 42 includes a first impeller 44 and a second impeller 46, where each impeller comprises a solid central shaft and helical rotor 45 and 47, respectively, formed over the shaft. The catheter body 42 has a distal end 48 and a proximal hub 50. The proximal hub 50 includes an aspiration port 52 connected to a lumen 60 (FIG. 1E) in which the first impeller 44 is disposed. The hub 50 has a second infusion port 54 which is connected to lumen 62 (FIG. 1E) in which the second impeller 46 is disposed. The impellers 44 and 46 have drive connectors 56 and 58 at their proximal ends. The drive connectors may be connected to suitable drive unit(s) for rotation of the impellers in a desired direction. The catheter body also includes a separate guidewire lumen 64 to permit introduction of the material transport catheter 40 over a guidewire in a conventional manner. The catheter 40 may used by infusing a material through port 54, usually under pressure, with the assistance of the second impeller 46. That is, the second impeller will be rotated in the direction which causes the rotor 47 to advance material through the lumen 62 in a distal direction. Similarly, a material may be aspirated through the lumen 60 by rotating rotor 44 in a direction which transports the materials proximally through the lumen. Aspiration is optionally assisted by applying a vacuum to the port 52. The infusion and aspiration may be performed sequentially, simultaneously, or both at various points during a particular procedure. In particular, the catheter 40 may be used to circulate a thrombolytic or other therapeutic material to a target site and thereafter withdraw lysed or other treated materials from that target site without the need to remove or exchange the catheter.

Figure 2:
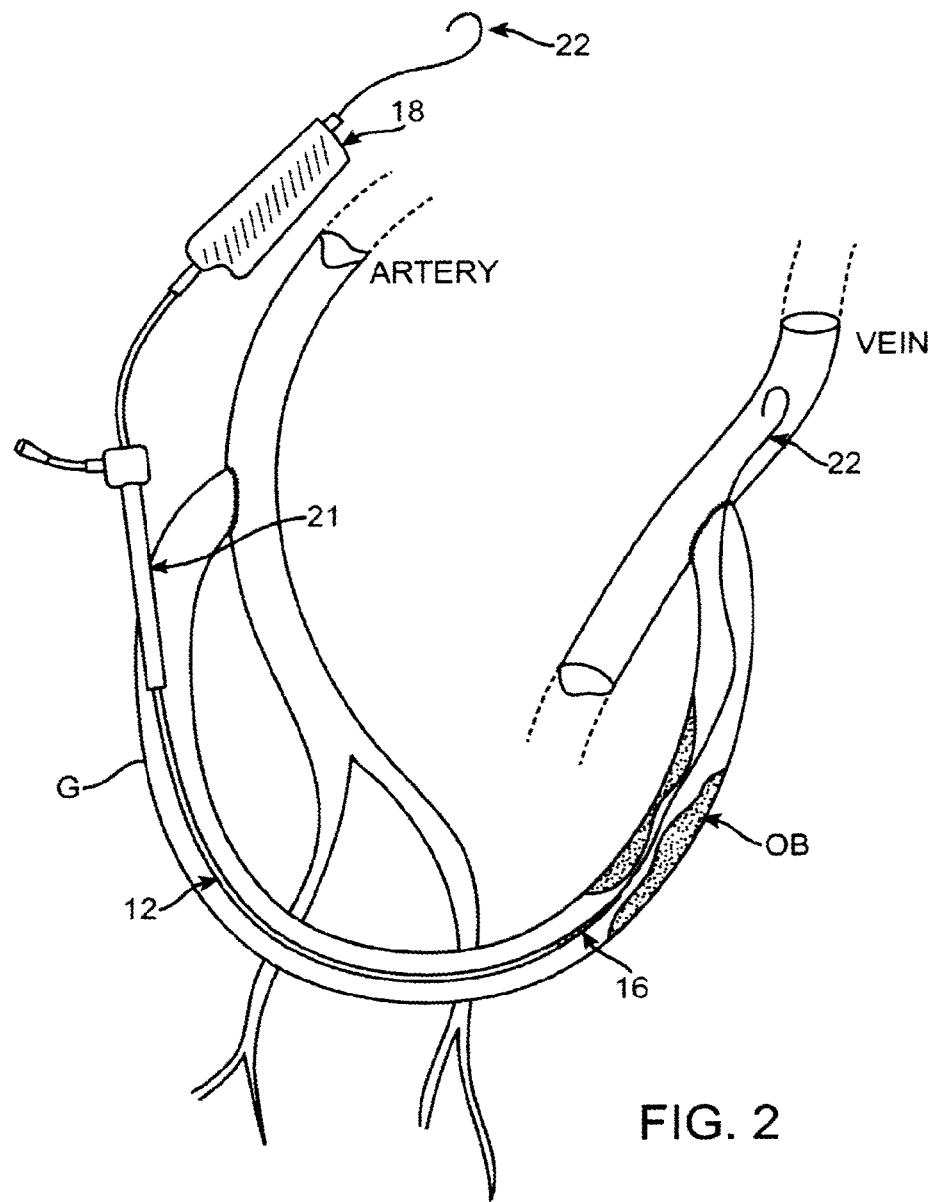
FIG. 2 illustrates use of the material transport catheter of FIG. 1 in performing an infusion/aspiration procedure according to the methods of the present invention over a guidewire.

In operation, as depicted in FIG. 2, the aspirating catheter 10 is percutaneously inserted through an introducer sheath 21, and into the lumen of the vessel or synthetic graft from which material is to be removed. In the example shown, the aspirating catheter 10 is inserted into an arterio-venous dialysis graft G, and tracked over a guidewire 22 to the area containing thrombus or obstructive matter OB. A motor drive unit 18 is then activated to rotate the impeller 16. At the point the aspirating catheter comes into contact with the material to be removed, the material is pulled into the lumen of the catheter body and funneled or pumped proximally by the rotor as it rotates within the catheter lumen.

Figure 3A:
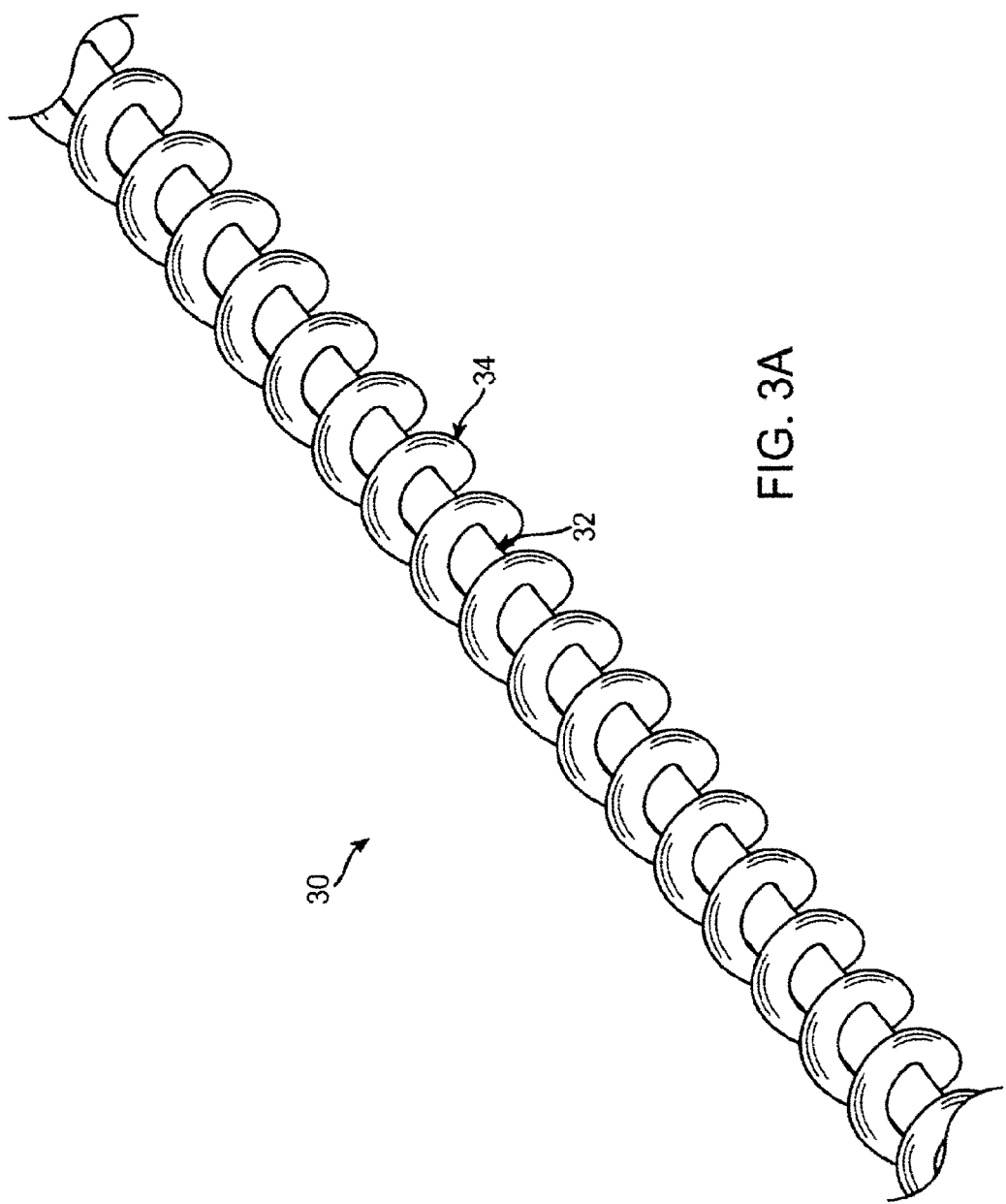
FIGS. 3A-3D illustrate the components of a mechanical pump constructed in accordance with the principles of the present invention.
Figure 3B:
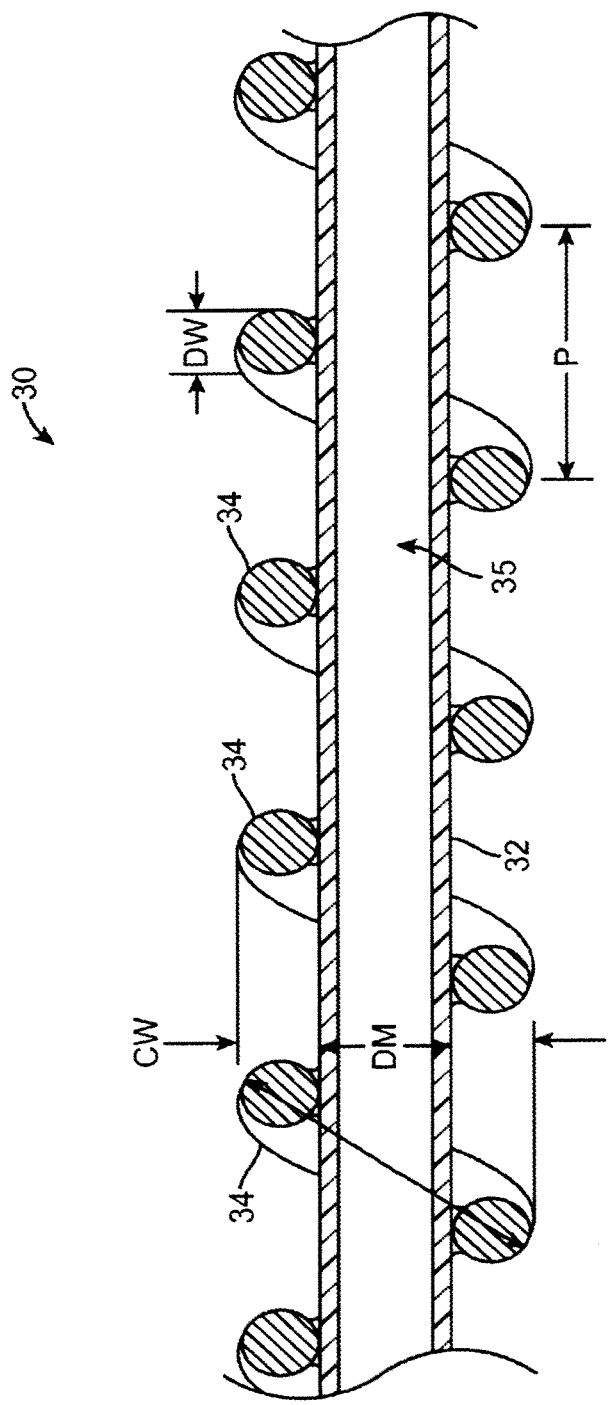

Detailed construction of an exemplary impeller 30 is shown in FIGS. 3A and 3B. Inner tube 32 is formed of a flexible polymer material, preferably a polyimide, but can also be made from any thermoplastic, for example polyethylene or nylon or a thermoset, for example urethane. In some cases, it would be possible to form the inner tube from a flexible metal, such as a shape memory alloy, as Nitinol® alloy. The inner tube 32 is either extruded as a hollow tube, or formed around a mandrel (not shown), to create a central guidewire lumen 35 (FIG. 3B). Optionally, in order to enhance the torqueability of the shaft, it may be desirable to form the inner tube as a braid coil, stacked coil, or coil-reinforced extrusion. Suitable coils for forming the inner tube may be constructed as multi-filar coils, counterwound filament coils, or stacked filament coils. The filaments forming the coils may be composed of metals or polymers. In the preferred embodiment, inner tube 32 has an outer diameter in the range of 0.02 inch (0.5 mm) to 0.06 inch (1.5 mm), preferably 0.04 inch (1 mm), and an inner (central lumen) diameter in the range of 0.015 inch (0.38 mm) to 0.045 inch (1.1 mm) to accommodate various common sizes of guidewires through the central lumen, preferably and an inner diameter of 0.021 inch (0.533 mm) to accommodate a 0.018 inch (0.46 mm) guidewire. A resilient coil 34 is wrapped over the outer surface of the inner tube 32 to a desired length, preferably over at least a major portion of the length of the inner tube, usually over at least 50% of the inner tube length, more usually at lest 75%, and most often at least 90% or more, and often running coextensive therewith.

Resilient coil 34 may be a single filament structure, a multiple filament structure, a plurality of filaments, a multi-filar structure, or the filaments may be a round wire, a ribbon wire, or a wire having an irregular cross-section, further where the filaments may have the same diameter, different diameters, and/or may be stacked. The coils will usually be a metal, but could also be formed from a variety of polymers. The exemplary coil 34 is formed of a round wire, preferably an 0.014 inch (0.36 mm) diameter 304 stainless steel wire, but can also be formed from Nitinol® alloy (NiTi), Elgiloy® or Titanium. Alternatively, it could be formed from a high durometer polymer or polymer fiber with a higher melt temperature than inner tube 32, such as PEEK or Kevlar®. In an alternative embodiment, coil 34 may have a geometric cross sectional shape other than round, such as oblong, triangular, or square.

The pitch of the resilient coil 34 can also be defined in terms of the distance between successive turns of the coil or still further alternatively, as the "turns/cm." A table setting forth all the pertinent dimensions of the exemplary impeller 31, including the alternative pitch dimensions, is set forth below.

TABLE I

EXEMPLARY DIMENSIONS

|  | Broad | Narrow |
|---|---|---|
| Inner Tube 32 | | |
| Outer Diameter $D_M$ | 0.5 mm to 5 mm | 1 mm to 2 mm |
| Inner Diameter $D_I$ | 0.4 mm to 2.9 mm | 0.5 mm to 1.9 mm |
| Length | 5 cm to 250 cm | 45 cm to 125 cm |
| Coil 34 | | |
| Diameter $D_W$ | 0.02 mm to 2.5 mm | 0.15 mm to 0.5 mm |
| Pitch P | 0.2 mm to 10 mm | 1 mm to 4 mm |
| (turns/cm) | 1 to 50 | 3 to 10 |
| Coil Assembly Width $C_W$ | 0.5 mm to 10 mm | 0.5 mm to 3 mm |

Figure 3C:
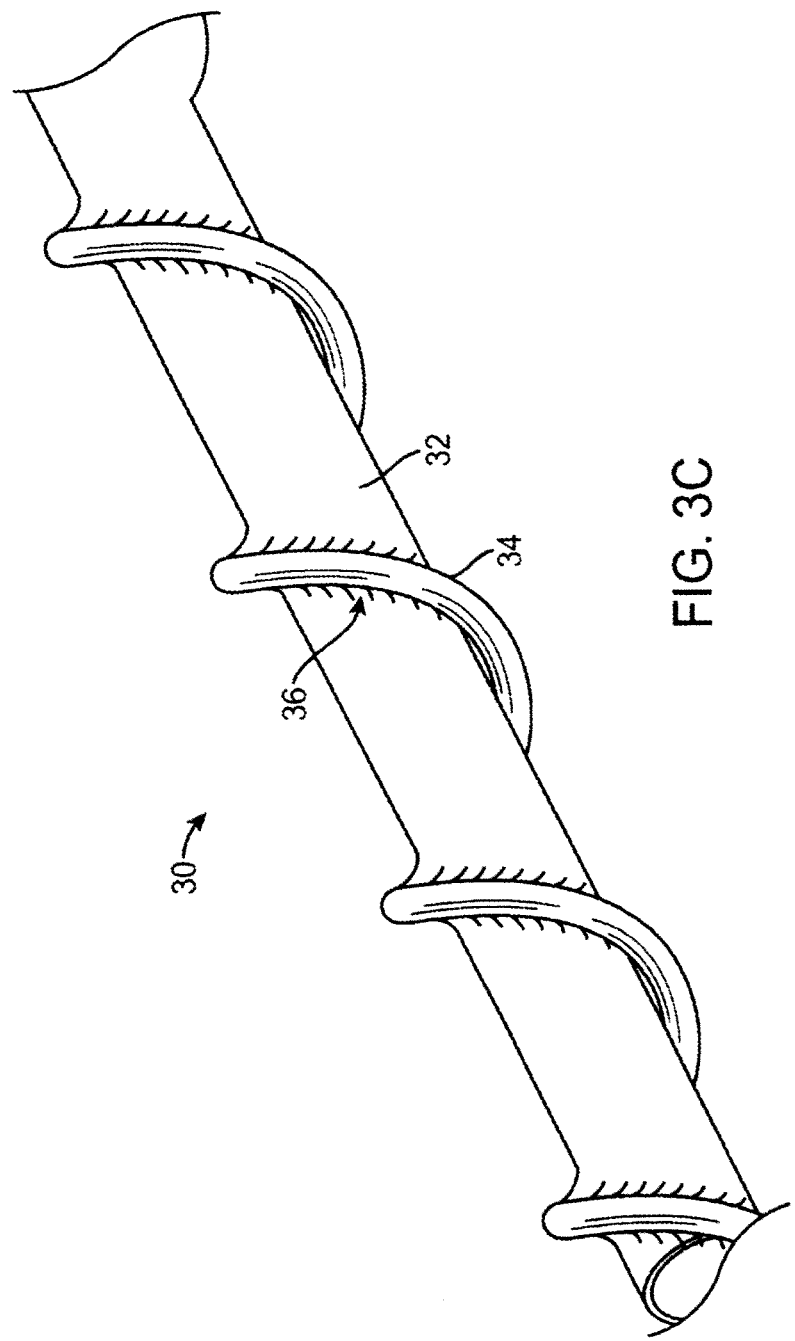

As illustrated in FIG. 3C, an outer jacket 36 is formed over the inner tube 32 and rotor 34 of the impeller 30, usually by dip coating the tube 32. The coated assembly is then subjected to heat bonding or cross-linking to adhere the outer coating 36 with the inner tube 32, thereby encapsulating coil member 34. The jacket coating is preferably made of the same material as is chosen for the inner tube 32 or other material capable of heat bonding or cross-linking therewith, such as nylon, polyamide, polyurethane, PTFE, FEP, and the like. Jackets formed by dip coating will have a much thinner wall thickness than inner tube measuring in the range of 0.001 inch to 0.002 inch. While the inner tube 32 has been illustrated as being a solid polymeric tube, in some instances it will be possible to utilize a coil as the inner tube. Placement of a jacket coating over the coil member 34 which forms the impeller and an inner member formed as a coil would help strengthen the inner coil member while still leaving it quite flexible.

Alternatively, the outer jacket 36 may be formed by other conventional techniques, such as heat shrinking a polymeric sheath or tube over the assembly of the inner tube 32 and coil 34, where the sheath material may be the same as or different than the underlying tube 32. Heat shrinking of a jacket would be particularly effective if the tube 32 is formed from a non-polymer, such as a shape memory metal alloy. In some cases, it might also be possible to extrude or spray the outer jacket 36 over the assembly of the inner tube 32 and rotor 34.

Figure 3D:
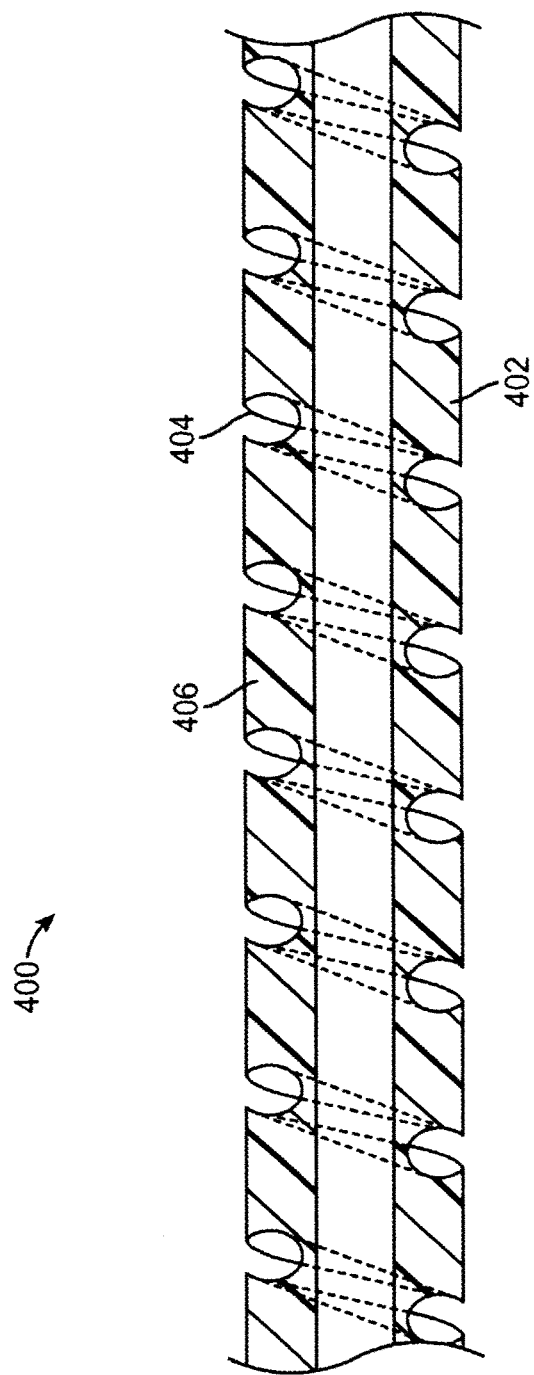

An impeller 400 (FIG. 3D) comprising a tubular member 402 has a helical channel 404 formed in its outer surface 406. The helical channel 404 may be formed by embedding a wire, ribbon, cable, small diameter tube, or other element that can be wrapped into a helical shape into the outer surface 404. When the embedded element is removed, the channel or groove 404 will be left in place. The resulting helical channel or groove 404 will act as the impeller surface as the impeller 400 is rotated as described elsewhere in this application. Thus, the combination of the helical groove 404 and remaining surface 406 of the impeller 400 will constitute the helical rotor described elsewhere herein in both the specification and claims.

Referring now to FIGS. 4A and 4B, impellers capable of bi-directional and enhanced material transport are illustrated. In FIG. 4A, a bi-directional impeller 60 comprises an inner tube 62 having the properties generally described above in connection with impeller 30. A first helical rotor 64 is formed over the outer surface of inner tube 32, again generally as described above for impeller 30. Bi-directional impeller 60 differs, however, in that it includes a second helical rotor 66 disposed in a central lumen 68 of the inner tube 62. The rotor 66 may generally have the same characteristics as described above for rotor 64, but will have a generally smaller diameter (so that it fits within the lumen) and will be wound in a direction opposite to that of the first rotor 64. Thus, the helical rotors 64 and 66 will be "counterwound" with respect to each other. By providing rotors which are counterwound, it will be appreciated that rotation of the impeller 60 within a lumen of a catheter body (not illustrated in FIG. 4A), will induce material transport in opposite directions. Material transport in a first direction may be achieved in the annular region between the outer surface of inner tube 62 and the inner surface of the luminal wall of the catheter body. In contrast, material transport flow through the central lumen 68 of the inner tube 62 will be in a direction opposite to that of flow in the annular space since the rotors 64 and 66 are wound in opposite directions. That is, if the helical rotor 64 has a right-handed coil direction, the second rotor 66 will have a left-handed coil direction.

Referring now to FIG. 4B, the use of first and second helical rotors on an impeller may also be used to provide enhanced or modified material transport flow in a single direction. Impeller 70 includes an inner tube 72, a first helical rotor 74, and a second helical rotor 76. Construction of the impeller 70 may be very similar to that of impeller 60, except that the first helical rotor 74 and second helical rotor 76 will be wound in the same direction. The pitches and specific dimensions of the helical rotors may vary from each other, and may vary along their lengths, but they will both be configured to deliver material through a catheter lumen in the same direction when the impeller is rotated in either direction. Such a design has many potential advantages. First, it can provide for higher volumetric and mass flows then is achievable when the second rotor 76 is absent. It can provide for different flow rates to different portions of the catheter. It can permit two different streams of the same or different materials to be delivered to a single or multiple locations within the catheter. It could also be useful to provide a mixing catheter where two different fluids are delivered and the mixed in situ at the distal end of the catheter. The latter is particularly advantageous for chemicals and reagents that cannot be pre-mixed prior to delivery.

Impeller 60 has other advantages. By providing for bi-directional flow using a single impeller, circulation and recirculation of materials to a target site within a patient body lumen may be achieved. For example, a thrombolytic agent could be introduced through the central lumen 68 of the impeller 60 while lysed clot, thrombus, or other occlusive materials are aspirated from the same target location in the annular lumen formed over the impeller. Other uses and advantages of the system will also be found.

Figure 5:
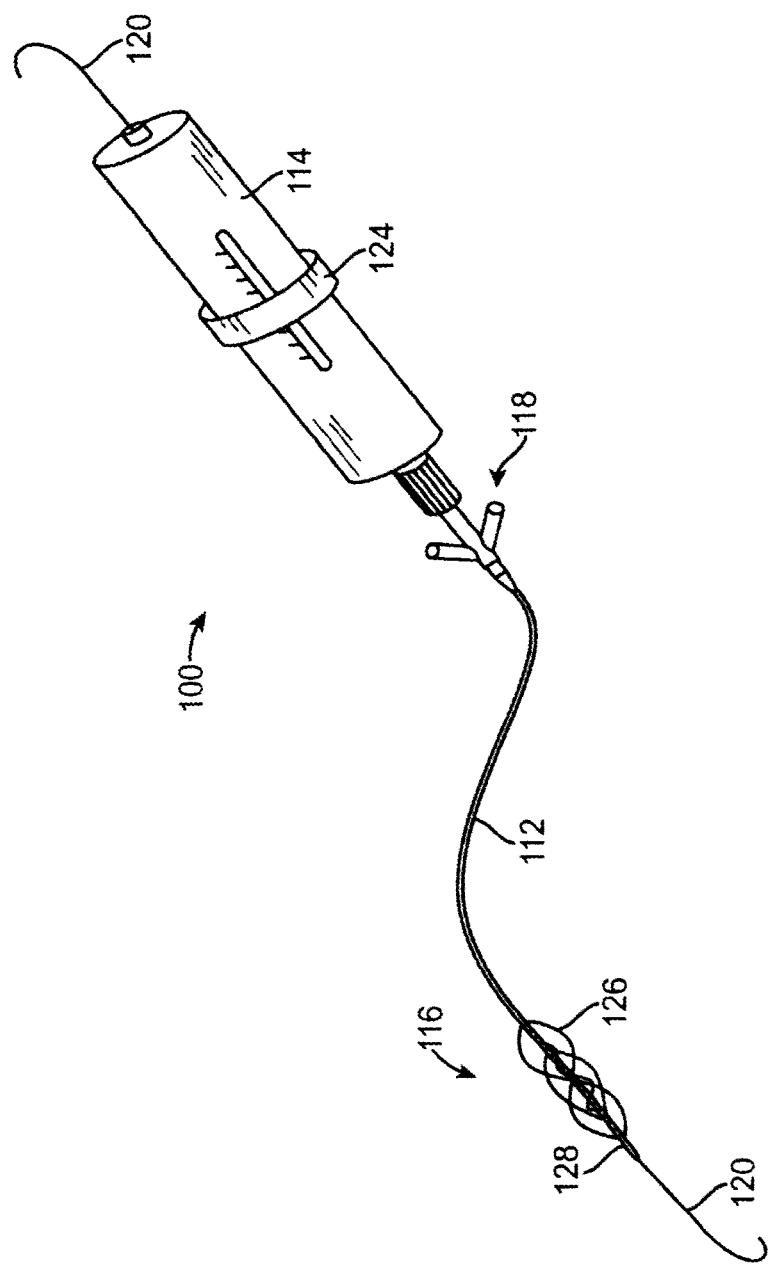
FIG. 5 is a perspective view of a clot disruption catheter system constructed in accordance with the principles of the present invention and employing a mechanical pump as part of a material transport mechanism.

Referring now to FIG. 5, a clot disruption system 110 constructed in accordance with the principles of the present invention will be described. The clot disruption system 110 includes a clot disruption catheter 112 and a motor drive unit 114. The catheter 112 has a distal section 116 which comprises an expansible cage and macerator components of the catheter, as described in greater detail in connection with FIGS. 5A and 5B. A proximal hub 118 is secured to the proximal end of the catheter 112 and removably connectable to the motor drive unit 114. The motor drive unit 114 will be configured to transmit rotational and/or axial translational forces through a tubular shaft 122 (FIGS. 5A and 5B) to manipulate the macerator. A slidable ring 124 is shown schematically on the motor drive unit 114 and is intended, for example, to permit axial translation of the macerator. Such axial translation, however, is not essential and is only an optional feature of the present invention.

Figure 5A:
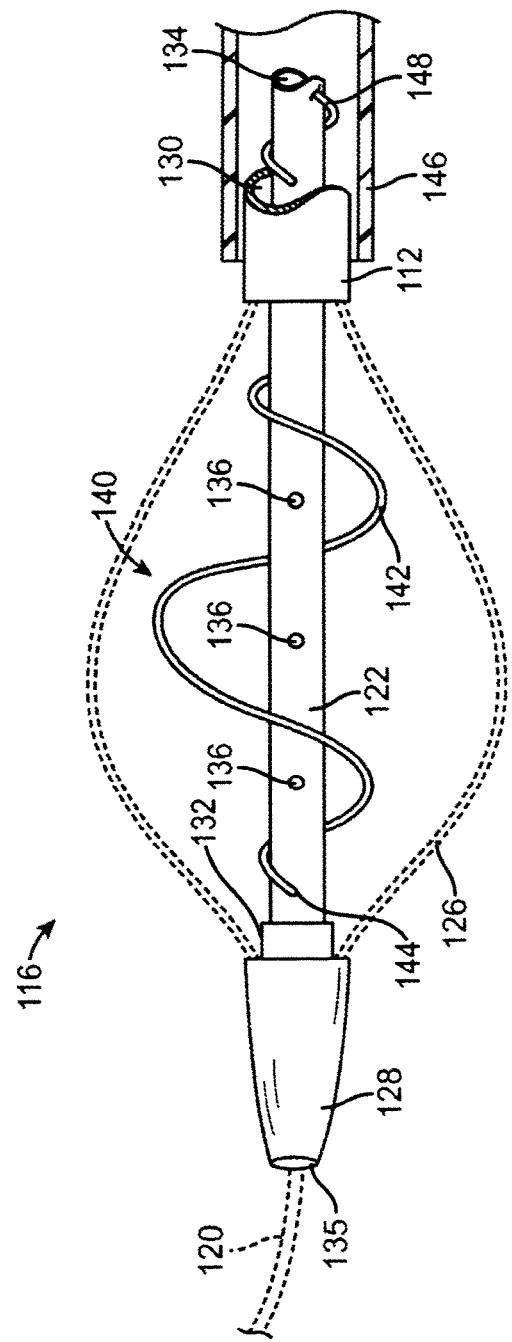
FIG. 5A is a detailed view of the distal end of the clot disruption catheter system of FIG. 5, with portions broken away.

The distal section 116 of the clot disruption catheter 112 is best illustrated in FIG. 5A. The distal section 116 comprises a radially expansible cage 126 which may have any of the forms and structures described above. In particular, cage 126 may comprise a plurality of helical wires or other elements. Alternatively, the cage may comprise a plurality of straight, axially aligned wires or other elements. The expansible cage 126 will be self-expanding, i.e., it will assume its radially expanded configuration absent any constraining forces, although it could utilize active means for expansion in other embodiments. The cage 126 is shown in its expanded configuration in FIGS. 1 and 5A. The distal tips of the cage elements are attached to a nose cone 128 which may be fixed or floating relative to the main portion of the catheter body 112, as described in more detail below.

The body of clot disruption catheter 112 will have a lumen 130 extending from hub 118 to the distal section 116, and the tubular shaft 122 will be disposed within the lumen 130. A distal end 132 of the tubular shaft 122 will be connected to the nose cone 128, and the shaft will preferably have an inner lumen 134 which terminates in a series of infusion ports 136 (which may be circular, as illustrated or may be elongate slits or may have a variety of other geometries) disposed between the distal end of the body of catheter 112 and the nose cone 128. The lumen 134 and infusion ports 136 will be useful, for example, for delivering thrombolytic and other agents used in connection with clot disruption. The lumen will also be able to receive a guidewire 120 (not shown) which exits through distal port 135 to facilitate positioning within a blood vessel or other body lumen.

Macerator 140 is disposed on the tubular shaft 122 within the expansible cage 126. The macerator 140 is illustrated as a helical wire or filament, but could comprise a variety of other structures. Helical wire 142 is formed from spring material, typically a spring stainless steel or shape memory alloy, and is fixedly attached to the shaft 122 at both ends. First attachment point 144 is visible in FIG. 5A, while the second attachment point is hidden behind the shaft. With this configuration of wire 142, it will be appreciated that the macerator 140 is self-expanding. Radial compression forces will cause the element 142 to collapse radially inwardly against the exterior of shaft 122.

Macerator 140 comprising helical wire 142 is intended to operate by rotation of the shaft 122. When the shaft 122 is rotating, the helix will trace a generally ovoid shell within the expansible cage 126, thus engaging and disrupting occlusive material which is within the cage. Optionally, although not necessarily, the macerator 140 may be configured to engage at least a portion of an inner surface of the expansible cage 126. In particular, when treating clot within blood vessels, the helical wire 142 will disrupt the clot and engage and entangle materials within the clot, particularly fibrin fibers which make up a substantial portion of the clot material. By breaking up and engaging the clot in this fashion, the clot is pulled away from the blood vessel wall rather than sheared from the wall as in many prior thrombectomy and atherectomy procedures. In particular, the combination of the expansible positioning cage 126 and the macerator which is spaced radially inward from the shell defined by the cage, clot removal and disruption can be performed with minimum risk of injury to the blood vessel wall.

The expansible cage 126 and macerator 140 will usually be radially collapsed to facilitate introduction and withdrawal of the catheter 112 to and from a target site within the vasculature or other body lumen. The necessary radial constraint can be provided in a number of ways. For example, a tether or filament could be wrapped around both the cage 126 and the macerator 140, with the constraint being removed when the device reaches the target site. Alternatively, the cage 126 and/or the macerator 140 could be composed of a heat memory material, permitting deployment by use of an induced temperature change, e.g., by passing an electrical current through the structures or by infusing a heated or cooled fluid past the structures. Preferably, however, a radial constraint will be provided by a sheath 146 which can be axially advanced to radially collapse both the cage 126 and macerator 140.

The catheter 112 further comprises a mechanical pump to assist in the removal of disrupted clot and other debris which is produced by operation of the macerator. The mechanical pump may comprise a helical rotor 148 which is disposed over the outer surface of the tubular shaft 122, as illustrated in both FIGS. 5A and 5B. Preferably, although not necessarily, the helical rotor 148 will extend from the proximal side of the macerator (helical wire 142) all the way into the interior of the hub 118. In this way, disrupted clot on other fluid materials can be pumped proximally by the rotor 148 (which acts as an "Archimedes screw") as the macerator and tubular shaft are rotated.

Figure 5B:
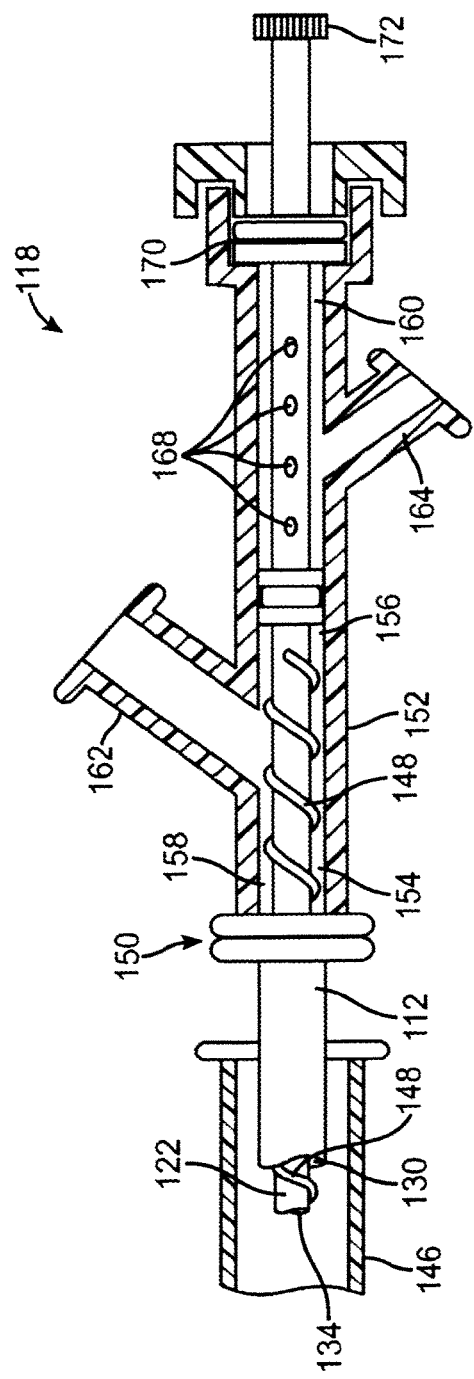
FIG. 5B is a detailed view of a portion of the proximal end of the clot disruption catheter of FIG. 5, with portions broken away.

Referring now to FIG. 5B, the construction of proximal hub 118 will be described. A rotating hemostatic fitting 150 is provided at the proximal end of catheter 112 and mates with the distal end of hub body 152. Tubular shaft 122 passes from the lumen 130 of catheter 112 into the interior 154 of hub body 152. A rotating hemostatic seal structure 156 is also provided within the interior 154 and divides the interior into a first isolated region 158 and a second isolated region 160. The first isolated region 158 has connector branch 162 which permits aspiration of fluids and materials through the lumen 130 of catheter 112. A second connector branch 164 opens to the second isolated region 160 and permits infusion of therapeutic agents, such as thrombolytic agents, into the lumen 134 of the tubular shaft 122 through ports 168. A rotating seal 170 is provided at the proximal end of the hub and a hemostatic valve 172 is provided on the proximal end of tubular shaft 122 to permit introduction of a guidewire. The connector 172 will also be suitable for coupling to the motor drive unit 114 (FIG. 5) to permit rotation of shaft 122 which in turn rotates the macerator 140. Note that the hub 118 illustrated in FIG. 5B is not suitable for axial translation of the shaft 122 relative to the catheter 112.

Figure 6:
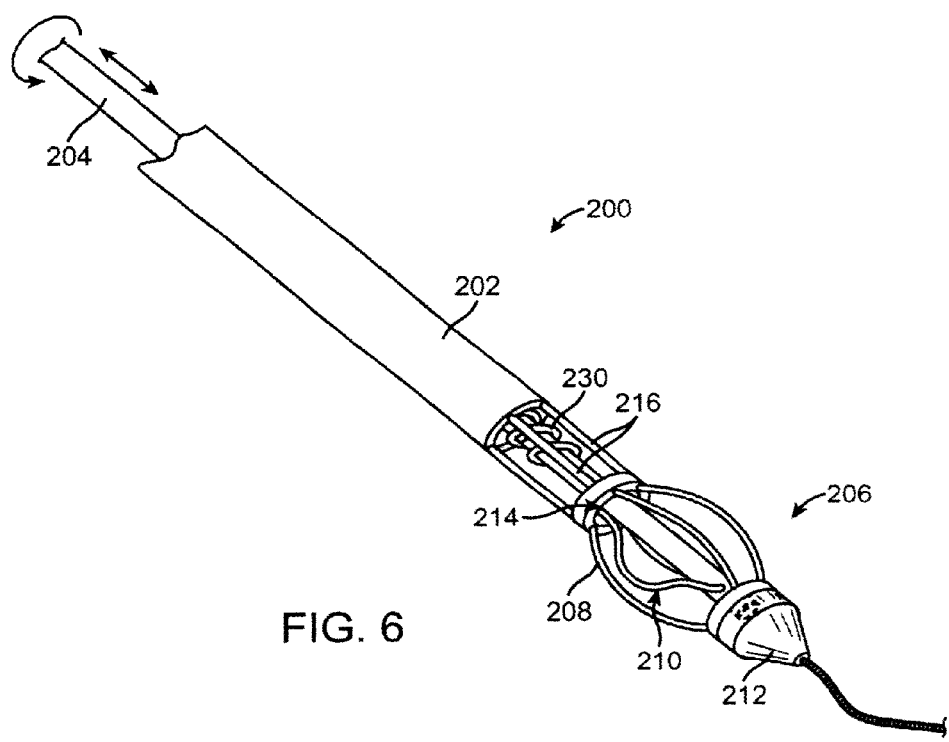
FIGS. 6, 6A, and 6B illustrate a second exemplary clot disruption catheter constructed in accordance with the principles of the present invention and employing a material transport mechanism.
Figure 6A:
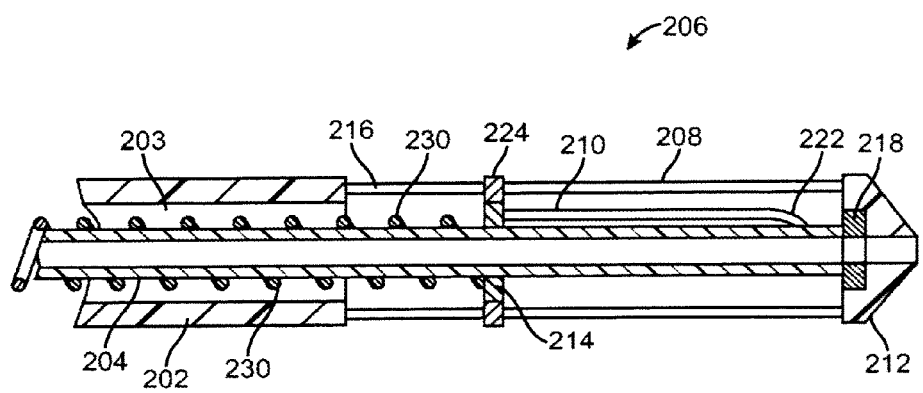
Figure 6B:
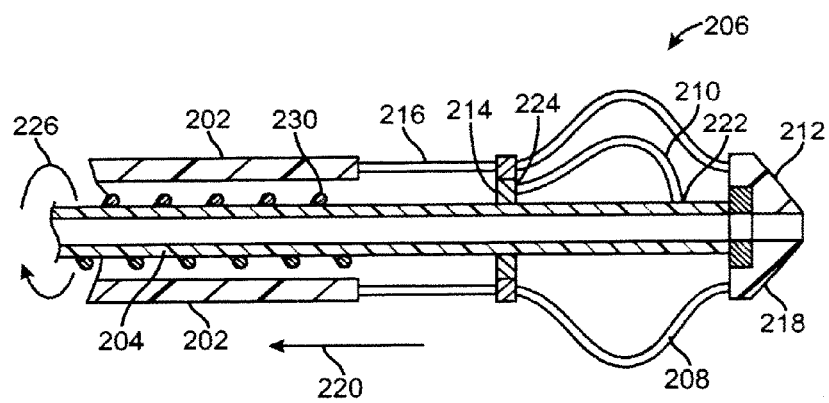

Referring now to FIGS. 6, 6A and 6B, a second exemplary clot disruption catheter 200 will be described. The catheter 200 includes a catheter body 202 and a tubular shaft 204 which is rotatably and axially slidably received in a lumen of the catheter body. The catheter 200 has a distal section 206 including a radially expansible cage 208 and a macerator 210 in the form of an arcuate wire. In contrast to catheter 112 of the first embodiment, both the expansible cage 208 and macerator 210 will be selectively and controllably expansible in the clot disruption catheter 200.

Referring in particular to FIGS. 6A and 6B, the tubular shaft 204 extends through lumen 203 of the catheter body 202 and terminates in a nose cone 212. A bearing structure 214 receives the tubular shaft 204 and permits both rotation and axial translation thereof relative to the catheter body 202. While the bearing 214 could be positioned directly on the distal tip of the catheter body 202, that would block lumen 203 and prevent collection of disrupted clot or other occlusive material therein. Thus, it is desirable to mount the bearing structure 214 distal to the distal end of catheter body 202, e.g., on spacer rods 216, to provide an opening or gap which permits aspiration of disrupted clot or other material through the lumen 203. The distal end of tubular shaft 204 is mounted in a second bearing structure 218 located in the nose cone 112. Bearing structure 218 permits rotation but not axial translation of the shaft 204. Thus, when the shaft 204 is drawn proximally in the direction of arrow 220 (FIG. 6B), the distance between the nose cone 212 and the bearing structure 214 is reduced. This causes the elements of cage 208 to axially shorten and radially expand. While the elements of cage 208 are shown as axial wires or filaments, it will be appreciated that they could be helical or have any one of a variety of other configuration which would permit radial expansion upon axial contraction. Similarly, the macerator wire 210 is fixedly attached to the tubular shaft 204 at an attachment point 222. The other end of the macerator wire 210 is connected at attachment point 224 to the portion of bearing structure 214 which rotates together with the tubular shaft 204. In this way, the macerator is both axially shortened so that it radially expands and is able to rotate when the tubular shaft 204 is rotated, e.g., in the direction of arrow 226.

The clot disruption catheter 200, the clot includes a mechanical pump component to assist in extraction of clot or other disrupted materials through the lumen of the catheter. As best seen in FIGS. 6A and 6B, the mechanical pump comprises a simple helical screw, such as a helically wound wire or other element 230. Such a helical screw pump is commonly referred to as an "Archimedes" screw pump and operates by creating a vertical flow as the screw pump is rotated. While in some instances use of the screw pump may be sufficient in itself to remove materials, the screw pump will most often be used in combination with vacuum aspiration to remove materials through the lumen of the catheters.

Figure 7A:
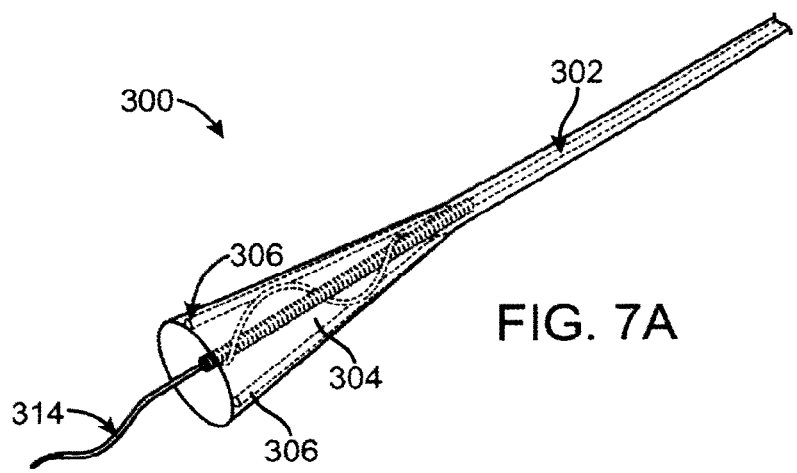
FIGS. 7A and 7B illustrate the distal portion of a third embodiment of a clot disruption catheter constructed in accordance with the principles of the present invention and employing a material transport mechanism.
Figure 7B:
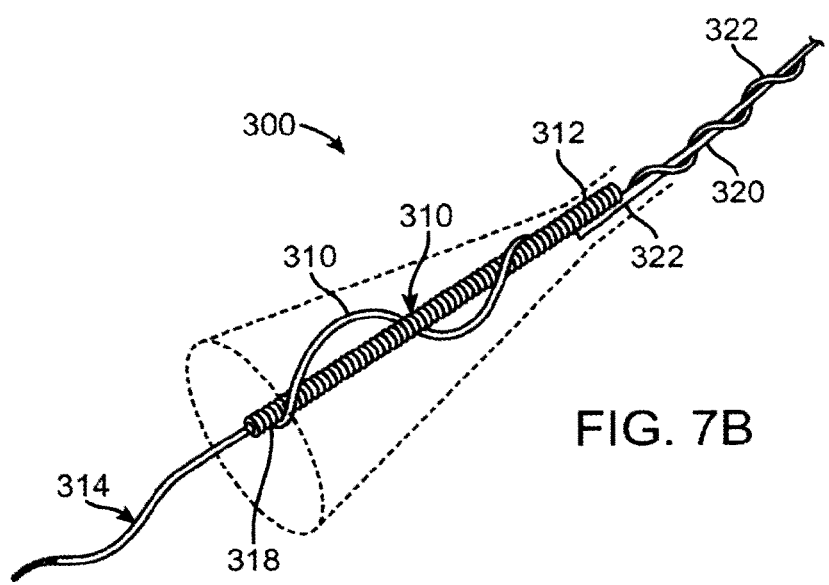

An additional exemplary clot disruption catheter 300 is illustrated in FIGS. 7A and 7B. The clot disruption catheter 300 comprises catheter body 302 having an expansible cage 304 at its distal end. In contrast to previous embodiments, the expansible cage 304 is in the form of a conical "funnel" which may be formed from impervious materials (which will not permit the bypass of blood or other luminal flows) or from "filtering" materials which will permit blood or other bypass flows. Preferably, the funnel will be formed from pervious materials, such as wire meshes, perforate membranes, woven fabrics, non-woven fabrics, fibers, braids, and may be composed of polymers, metals, ceramics, or composites thereof. The filters will have a pore size selected to permit blood flow (including blood proteins) but capture disrupted clot and other embolic debris. Useful pore sizes will be in the range from 20 µm to 3 mm.

The funnel will usually be formed from a flexible filter material and supported on a plurality of rods 306 which can be actively or passively deflected in order to open or close the conical cage. Most simply, the rod members 306 will be resilient and have a shape memory which opens the cage structure in the absence of radial constraint. Thus, catheter 300 may be conveniently delivered through a sheath, in a manner analogous to that described in connection with FIG. 5. The clot disruption catheter 310 further includes a macerator assembly 310, best observed in FIG. 7B. The macerator comprises a tubular shaft 312, such as a highly flexible coil shaft adapted to transmit rotational torque. Tubular shaft 312 will include an internal lumen to permit introduction over a guidewire 314. A helical macerator wire 316 has a distal end 318 attached to the distal end of shaft 312. A proximal portion 320 of the macerator 316 extends through a tube 322 attached to the side of the tubular member 312. In this way, the helical portion of macerator 316, which has a helical memory shape, can be expanded and contracted by axially translating the proximal portion 320. Although illustrated passing through a separate tubular member 22, the proximal portion 320 could pass through the same lumen of the tubular shaft 316 as does the guidewire 314. It will be appreciated that the macerator structure 316 could be employed with any of the previous embodiments where it is desired to provide for selective expansion and contraction of the macerator.

The proximal portion 320 of the macerator 316 will comprise a helical rotor 322 to form an impeller as described in connection with previous embodiments of the material transport catheters of the present invention. The impeller will act to assist in the aspiration of materials macerated by the macerator 310 and collected in the funnel 304, typically in combination with application of a vacuum at the proximal end of the catheter 300 (not shown).

Figure 8:
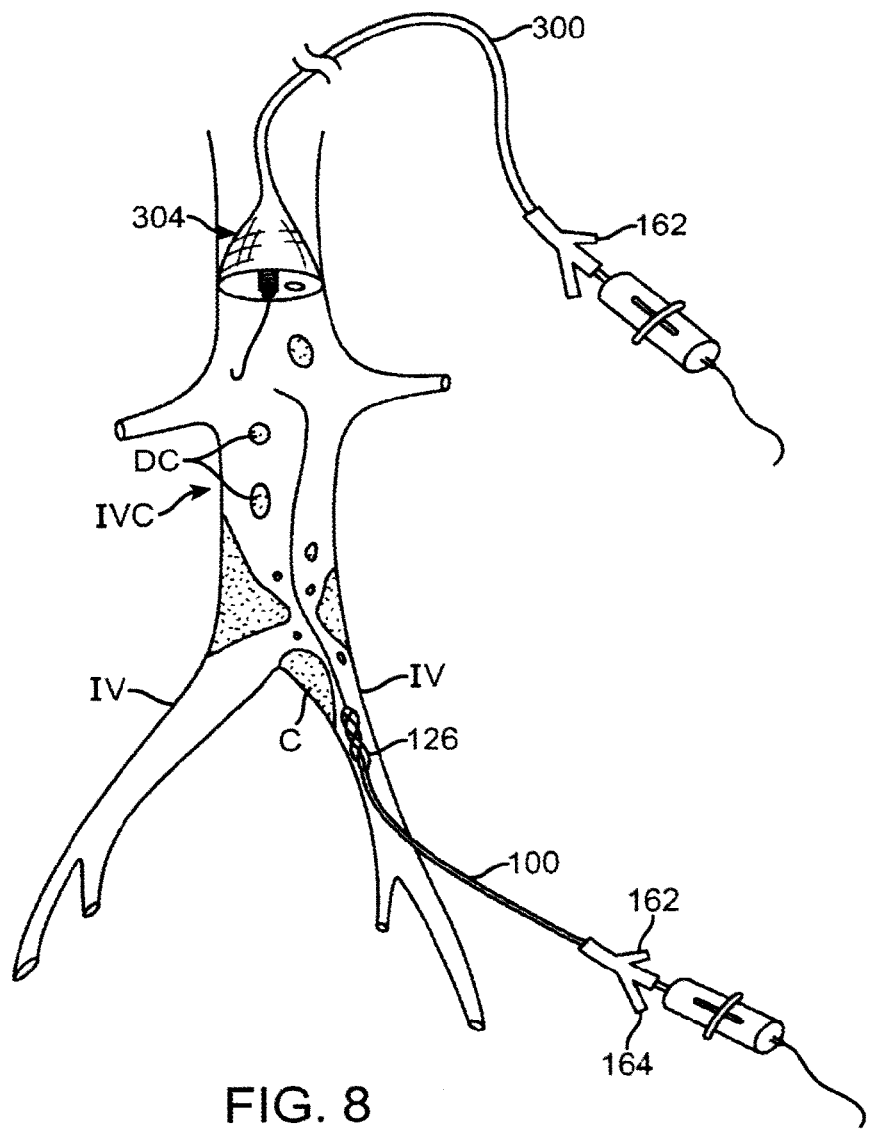
FIG. 8 illustrates use of the catheters of FIG. 5 and FIGS. 7A and 7B in combination.

Referring now to FIG. 8, use of clot disruption catheter 200 and clot disruption catheter 300 for performing a procedure in accordance with the principles of the present invention will be described. The catheters 200 and 300 are introduced to a region within the patient's venous system, e.g., at the junction between the iliac veins IV and the inferior vena cava IVC. Blood flow is in the direction from bottom to top, and catheter 200 is introduced into the iliac vein IV in an antegrade direction, i.e., in the direction of blood flow. Catheter 300 is introduced into the inferior vena cava IVC in a retrograde direction, i.e., against the flow of blood. Filtering cage 304 is expanded so that the distal end of the "funnel" engages and generally seals around the interior wall of the inferior vena cava. Positioning cage 126 on catheter 200 is advanced into a region of clot C within the iliac vein IV and the macerator (not shown) is activated in order to disrupt the clot. Mechanical pumping and optionally aspiration will be applied through port 162 in order to draw a portion of the disrupted clot out of the patient's vasculature. Further optionally, a thrombolytic agent may be introduced through port 164. Pieces of the disrupted clot DC, however, may be released into the blood flow so that they pass from the iliac vein IV into the inferior vena cava. By positioning the funnel-like cage 304 of catheter 300 within the inferior vena cava, however, the disrupted clot may be captured and, optionally, further disrupted using the macerator assembly within catheter 300. This material may then be aspirated through port 162, being transported using a mechanical pump as elsewhere described herein.

Figure 9:
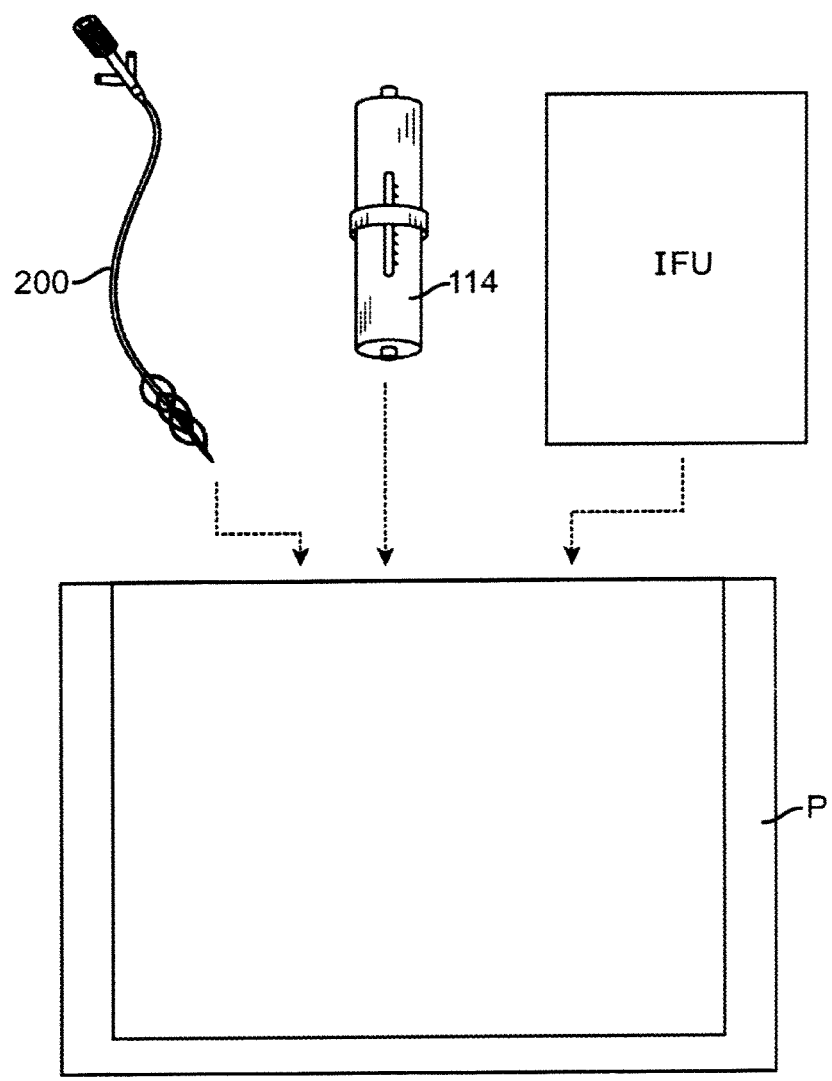
FIG. 9 illustrates a kit constructed in accordance with the principles of the present invention.

Turning now to FIG. 9, the present invention further comprises kits which include at least a catheter, which is shown to be catheter 200 but can be any other mechanical transport catheter in accordance with the methods of the present invention. The kit will further include instructions for use IFU setting forth any of the methods described above. Optionally, the kit may further comprise a motor drive unit 114 (particularly a dual direction drive unit) or other kit components, such as a guidewire, a thrombolytic agent, or the like. Usually, the kit components will be packaged together in a pouch P or other conventional medical device packaging, such as a box, tray, tube, or the like. Usually, at least the catheter component will be sterilized and maintained sterilely within the package. Optionally, the motor drive unit may not be included with the kits, but may instead be provided as a reusable system component. In that case, usually, the catheter will be disposable.

Figure 10:
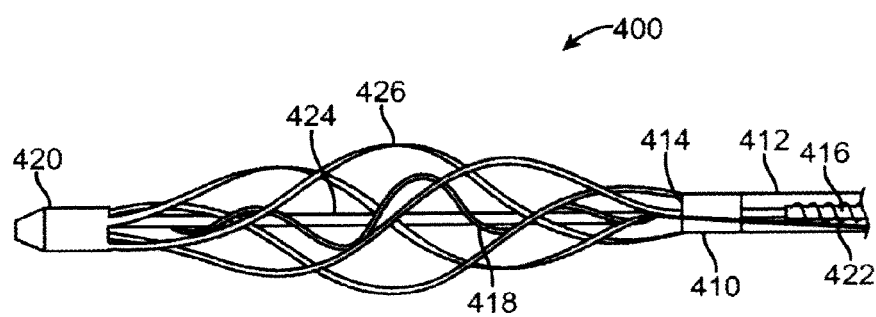
FIG. 10 illustrates a circulation catheter employing a clearing element in accordance with the present invention.

Now referring to FIG. 10, the present invention comprises a circulation catheter 400 having a clearing element 410. The catheter generally comprises a catheter body 412 having a lumen forming a distal opening 414 at the distal end of the catheter body. The circulation catheter also has an impeller 416 rotatably disposed in the lumen of the catheter body to aspirate materials from the distal end to the proximal end of the catheter body. The impeller 416 may comprise a coiled rotor 422 coupled to a shaft 424. The clearing element 410 is disposed at the distal opening 414 of the catheter body 412 to prevent the materials from accumulating at the opening and restricting flow.

The circulation catheter may further comprise a material capture device, such as a macerator 418 disposed at the distal end of the catheter body 412. The distal end of the macerator 418 is fixed to the shaft 424 at the catheter tip 420. The proximal end of the macerator 418 may extend unattached into the distal opening 414 of the catheter body to form the clearing element 410. In general, the clearing element 410 spins relative to the catheter body 412 to clear the distal opening 414 of the catheter body as the shaft 424 is rotated. The catheter 400 may also have an expansible cage 26 surrounding the macerator 418, wherein the macerator 418 engages the expansible cage as it is rotated.

Figure 11:
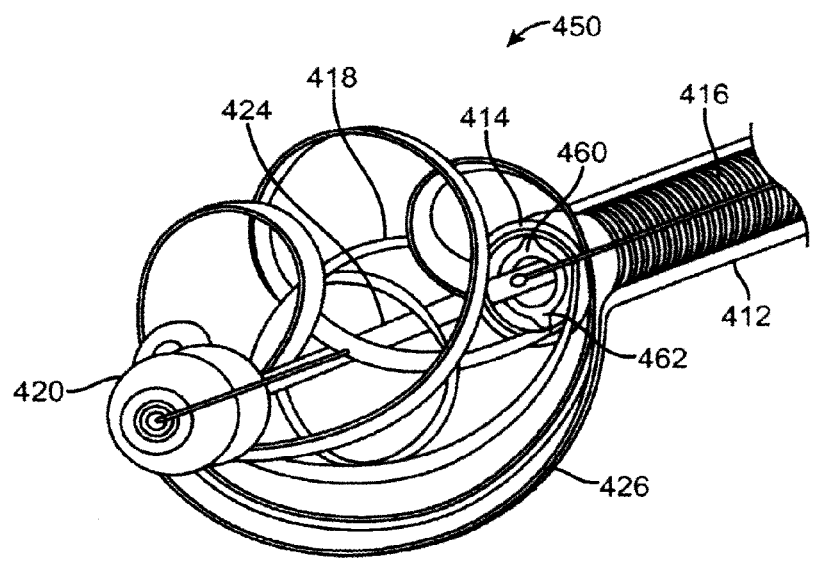
FIG. 11 illustrates an alternative circulation catheter having a cutting disk as a clearing element.

Now referring to FIG. 11, an alternative circulation catheter 450 has a clearing element comprising a cutting member 460 at or near the distal opening. The cutting member 460 may comprise any shape to facilitate clearing of the opening 414 when rotated about the catheter body 412, but generally comprises a thin, hollowed out disk with flanges 462 that are disposed to break up material as the cutting member is rotated. The cutting member 460 may be attached to the proximal end of the macerator 418. Alternatively, the cutting member may be attached to the shaft 424 or impeller 416.

While the above is a complete description of the preferred embodiments of the invention, various alternatives, modifications, and equivalents may be used. Therefore, the above description should not be taken as limiting the scope of the invention which is defined by the appended claims.

What is claimed is:

1. Apparatus for transporting material between a target site in a lumen of a body and a location external to the body, the apparatus comprising:
   an impeller including an elongate flexible tube defining a lumen, a coiled rotor element disposed over an outer surface of the tube, and a jacket securing the coiled rotor element to the outer surface of the tube;
   means for introducing the impeller to the target site; and
   means for rotating the coiled rotor element within the body lumen to advance the material proximally away from the target site.

2. The apparatus of claim 1, the impeller further comprising a macerator attached at a distal end of the coiled rotor element, wherein rotating the coiled rotor element further comprises rotating the macerator.

3. The apparatus of claim 1, the impeller further comprising a clearing element comprising a cutting disk attached to the coiled rotor element.

4. The apparatus of claim 1, wherein a distal portion of the coiled rotor element is unattached to the tube to provide a whip element as the coiled rotor element is rotated.

5. The apparatus of claim 1, wherein the tube has an outer diameter in the range from 0.5 mm to 5 mm, and the coiled rotor element has a pitch in the range from 1 to 50 turns/cm.

6. The apparatus of claim 1, further comprising a second coiled rotor element disposed within the lumen of the tube.

7. The apparatus of claim 6, wherein the first and second coiled rotor elements are counterwound.

8. The apparatus of claim 6, wherein the first and second coiled rotor elements are co-wound.

9. The apparatus of claim 1, wherein the tube comprises a braided tube, a mesh tube, a coil, a stacked coil, or a coil-reinforced polymer tube.

10. The apparatus of claim 9, wherein the coiled rotor element comprises a single filament, a multi-filar, stacked filaments, or multiple filament cable.

11. The apparatus of claim 10, wherein the filaments comprise a round wire, a ribbon wire, or a wire having an irregular cross-section.

12. A method for transporting material between a target site in a lumen of a body and a location external to the body, the method comprising:
   introducing a distal end of an impeller to the target site, the impeller including an elongate, hollow, flexible tube, a coiled rotor element disposed over an outer surface of the tube, and a jacket securing the coiled rotor element to the outer surface of the tube; and
   rotating the coiled rotor element within the body lumen to advance the material proximally away from the target site.

13. The method of claim 12, the impeller further comprising a macerator attached at a distal end of the coiled rotor element, wherein rotating the coiled rotor element further comprises rotating the macerator.

14. The method of claim 12, the impeller further comprising a clearing element comprising a cutting disk attached to the coiled rotor element.

15. The method of claim 12, wherein a distal portion of the coiled rotor element is unattached to the tube to provide a whip element as the coiled rotor element is rotated.

16. The method of claim 12, wherein the tube has an outer diameter in the range from 0.5 mm to 5 mm, and the coiled rotor element has a pitch in the range from 1 to 50 turns/cm.

17. The method of claim 12, further comprising a second coiled rotor element disposed within the lumen of the tube.

18. The method of claim 17, wherein the first and second coiled rotor elements are counterwound.

19. The method of claim 17, wherein the first and second coiled rotor elements are co-wound.

20. The method of claim 12, wherein the tube comprises a braided tube, a mesh tube, a coil, a stacked coil, or a coil-reinforced polymer tube.

21. The method of claim 20, wherein the coiled rotor element comprises a single filament, a multi-filar, stacked filaments, or multiple filament cable.

22. The method of claim 21, wherein the filaments comprise a round wire, a ribbon wire, or a wire having an irregular cross-section.

* * * * *